(12) United States Patent
Case

(10) Patent No.: US 6,989,269 B2
(45) Date of Patent: Jan. 24, 2006

(54) CELLS FOR DRUG DISCOVERY

(75) Inventor: Casey Case, San Mateo, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 252 days.

(21) Appl. No.: 10/412,105

(22) Filed: Apr. 10, 2003

(65) Prior Publication Data

US 2003/0175790 A1 Sep. 18, 2003

Related U.S. Application Data

(62) Division of application No. 09/779,233, filed on Feb. 8, 2001, now Pat. No. 6,689,558.
(60) Provisional application No. 60/181,117, filed on Feb. 8, 2000.

(51) Int. Cl.
*C12N 5/06* (2006.01)
*C12N 5/16* (2006.01)
*C12N 5/00* (2006.01)
*C12N 5/02* (2006.01)

(52) U.S. Cl. ........................................ 435/326; 435/375
(58) Field of Classification Search ................. 435/326, 435/375, 325
See application file for complete search history.

(56) References Cited

U.S. PATENT DOCUMENTS

| 4,980,281 | A | 12/1990 | Housey |
| 5,266,464 | A | 11/1993 | Housey |
| 5,298,429 | A | 3/1994 | Evans et al. |
| 5,580,721 | A | 12/1996 | Brent et al. |
| 5,580,722 | A | 12/1996 | Foulkes et al. |
| 5,688,655 | A | 11/1997 | Housey |
| 5,767,075 | A | 6/1998 | Avruch et al. |
| 5,789,538 | A | 8/1998 | Rebar et al. |
| 5,877,007 | A | 3/1999 | Housey |
| 6,007,988 | A | 12/1999 | Choo et al. |
| 6,013,453 | A | 1/2000 | Choo et al. |
| 6,140,081 | A | 10/2000 | Barbas |
| 6,140,466 | A | 10/2000 | Barbas et al. |
| 6,303,319 | B1 | 10/2001 | Rickles |

FOREIGN PATENT DOCUMENTS

| WO | WO 91/18980 | 12/1991 |
| WO | WO 93/06121 | 4/1993 |
| WO | WO 94/08051 | 4/1994 |
| WO | WO 95/12608 | 5/1995 |
| WO | WO 95/19431 | 7/1995 |
| WO | WO 95/30642 | 11/1995 |
| WO | WO 96/30540 | 10/1996 |
| WO | WO 98/54311 | 12/1998 |
| WO | WO 99/47656 | 9/1999 |
| WO | WO 00/23464 | 4/2000 |
| WO | WO 00/27878 | 5/2000 |
| WO | WO 00/41566 | 7/2000 |
| WO | WO 00/42219 | 7/2000 |

OTHER PUBLICATIONS

Beerli et al., "Toward Controlling Gene Expression at Will: Specific Regulation of the erbB–2/HER–2 Promoter by Using Polydactyl Zinc Finger Proteins Constructed From Modular Building Blocks," *Proc. Natl. Acad. Sci. U.S.A.* 95:1462–14633 (1998).

Choo et al., "In Vivo Repression by a Site–Specific DNA–Binding Protein Designed Against an Oncogenic Sequence," *Nature* 372:642–645 (1994).

Darling et al., "A zinc finger homeodomain transcription factor binds specific thyroid hormone response elements' molecular and cellular endocrinology.", *Mol. Cell. Endocrin.*, 139 (1–2):25–35 (1998).

Desjarlais & Berg, "Length–Encoded Multiplex Binding Site Determination: Application to Zinc Finger Proteins," *PNAS* 91:11099–11103 (1994).

Desjarlais & Berg, "Redesigning the DNA–binding specificity of a zinc finger protein: a data base–guided approach," *Proteins* 12: 101–104 (1992).

Hall et al., "Functional interaction between the two zinc finger domains of the v–erb A oncoprotein". *Cell Growth and Differentiation*, 3:207–216 (1992).

Kim et al., "A novel member of the RING finger family KRIP–a associates with the KRAB–A transcriptional repressor domain of zinc–finger proteins," *PNAS* 93:15299–15304 (1996).

Kim et al., "Design of TATA Box–Binding Protein/Zinc Finger Fusions for Targeted Regulation of Gene Expression," *PNAS* 94:3616–3620 (1997).

Klug, "Zinc Finger Peptides for the Regulation of Gene Expression," *J. Mol. Biol.* 293:215–218 (1999).

Liu et al., "Design of Polydactyl Zinc–Finger Proteins for Unique Addressing Within Complex Genomes," *PNAS* 94:5525–5530 (1997).

Liu et al., "Regulation of an Endogenous Locus Using a Panel of Designed Zinc Finger Proteins Targeted to Accessible Chromatin Regions: Activation of Vascular Endothelial Growth Factor A," *Journal of Biological Chemistry* 276(14):11323–11334 (2001).

Miller et al., "Repetitive Zinc–Binding Domains in the Protein Transcription Factor IIIA from *Xenopus Oocytes*," *EMBO J.* 4:1609–1614 (1985).

(Continued)

*Primary Examiner*—James Ketter
*Assistant Examiner*—Konstantina Katcheves
(74) *Attorney, Agent, or Firm*—Robins & Pasternak LLP; Sean M. Brennan

(57) ABSTRACT

Disclosed herein are compositions and method useful in screening a compound for its interaction and/or effect with a molecular target and/or cellular process.

22 Claims, 3 Drawing Sheets

OTHER PUBLICATIONS

Nolte et al., "Differing Roles for Zinc Fingers in DNA Recognition: Structure of a Six–Finger Transcription Factor IIIA Complex," *Proc. Natl. Acad. Sci. U.S.A.* 95:2938–2943 (1998).

Pavletich, N.P. & Pabo C.O., "Crystal Structure of a Five–Finger GLI–DNA Complex: New Perspectives on Zinc Fingers," *Science* 261:1701–1707 (1993).

Pavletich, N.P. & Pabo, C.O., "Zinc finger–DNA Recognition: Crystal Structure of a Zif268–DNA Complex at 2.1 A," *Science* 252:809–814 (1991).

Pomerantz et al., "Structure–Based Design of a Dimeric Zinc Finger Protein," *Biochemistry* 37(4):965–970 (1998).

Rhodes et al., "Zinc fingers," *Scientific American* 268:56–65 (1993).

Scheinman et al., "Characterization of Mechanisms involved in transfrepression of NF–kappa B by activated blucocorticoid receptors". *Mol. Cell. Biol.* ,15(2):943–953 (1995).

Zhang et al., "Synthetic Zinc Finger Transcription Factor Action at an Endogenous Chromosomal Site. Activation of the Human Erythropoietin G ne," *J. Biol. Chem.* 275:33850–33860 (2000).

PCR amplification scheme for production of ZFP-encoding synthetic genes.

CELLS FOR DRUG DISCOVERY

CROSS-REFERENCE TO RELATED APPLICATION

This application is a divisional of U.S. Ser. No. 09/779,233, filed Feb. 8, 2000 now U.S. Pat. No. 6,689,558 which in turn claims the benefit of provisional patent application Ser. No. 60/181,117, filed Feb. 8, 2000, from which priority is claimed under 35 U.S.C. § 119/120 and which applications are hereby incorporated by reference in their entireties.

TECHNICAL FIELD

This disclosure resides in the fields of cellular engineering and drug discovery.

BACKGROUND

Much of the research activity of pharmaceutical companies in years past focused on the incremental improvement of existing drugs. These efforts involved repetitive rounds of compound modification and biological testing and have resulted in a large percentage of the available drugs directed to similar targets.

Approximately a dozen years ago, the emphasis of pharmaceutical research activities began shifting toward the purposeful discovery of novel chemical classes and novel molecular targets. This change in emphasis, and timely technological breakthroughs (e.g., molecular biology, laboratory automation, combinatorial chemistry) gave birth to high throughput screening, or HTS, which is now widespread throughout the biopharmaceutical industry.

High throughput screening involves several steps: creating an assay that is predictive of a particular physiological response; automating the assay so that it can be reproducibly performed a large number of times; and, sequentially testing samples from a chemical library to identify chemical structures able to "hit" the assay, suggesting that such structures might be capable of provoking the intended physiological response. Hits from the high throughput screen are followed up in a variety of secondary assays to eliminate artifactual results, particularly toxic compounds.

A high throughput screen could involve the testing of 200,000 compound samples or more, therefore requiring the use of lab robots. Examples of samples tested in such an assay include pure compounds saved in compound archives (e.g., certain pharmaceutical companies have chemical libraries that have been generated through decades of medicinal chemistry effort), samples purchased from academic sources, natural product extracts and libraries purposefully created for high throughput screening such as combinatorial libraries.

The assays used in high throughput screens are intended to detect the presence of chemical samples possessing specific biological or biochemical properties. These properties are chosen to identify compounds with the potential to elicit a specific biological response when applied in vivo. High throughput screens typically identify drug candidates rather than the agents that will ultimately be used as drugs. A compound of a certain chemical class found to have some level of desired biological property in a high throughput assay can then be the basis for synthesis of derivative compounds by medicinal chemists.

The assays fall into two broad categories: biochemical assays and cell-based assays. Biochemical assays utilize pure or semi-pure components outside of a cellular environment. Enzyme assays and receptor binding assays are typical examples of biochemical assays. Cell-based assays utilize intact cells in culture. Examples of such assays include luciferase reporter gene assays and calcium flux assays.

Biochemical assays are usually easier to perform and are generally less prone to artifacts than conventional cell-based assays. Compounds identified as "active" in a biochemical assay typically function according to a desired mechanism, decreasing the amount of follow-up experimentation required to confirm a compound's status as a "hit." A major disadvantage of biochemical assays, however, is the lack of biological context. Compound "hits" from biochemical screens do not have to traverse a plasma membrane or other structures to reach and affect the target protein. Consequently, biochemical assays tend to be far less predictive of a compound's activity in an animal than cell-based assays.

Cell-based assays preserve much of the biological context of a molecular target. Compounds that cannot pass through the plasma membrane or that are toxic to the cell are not pursued. This context, however, adds complexity to the assay. Therefore conventional cell-based assays are much more prone to artifact or false positive results than are biochemical assays. Compounds that trigger complex toxic reactions or trigger apoptosis are particularly troublesome. Much of the labor devoted to conventional cell-based high throughput screening is directed to follow-up assays that detect false hits or hits that work by undesirable mechanisms.

If false positive or artifactual hits could be rapidly identified and eliminated, the ease and efficiency of biochemical assays could be approached in cell-based assays, while preserving the biological context. The result would be an assay with optimum throughput and optimum predictability of biological function. In short, a more efficient process for the discovery of new pharmaceuticals would be produced.

SUMMARY

In one aspect, methods of screening a compound for interaction with a molecular target are provided. In certain embodiments, the method involves the following steps: (a) contacting a first cell with the compound; (b) determining a first value of a property of the first cell, the property being responsive to the cell being contacted with the compound; (c) contacting a second cell with the compound, wherein the second cell comprises an exogenous zinc finger protein that directly or indirectly modulates expression of the molecular target; (d) determining a second value of the property in the second cell. A difference between the value of the cell property in the first cell and the cell property in the second cell provides an indication of an interaction between the compound and the molecular target. The zinc finger protein preferably modulates expression of the molecular target itself, but, in some embodiments, may indirectly modulate expression of the molecular target for example, by modulating expression of a protein that then modulates and/or affects the molecular target. Therefore, using these screening methods, one can, for example, test a compound for its capacity to transduce a signal through the molecular target or its capacity to block transduction of a signal through the molecular target.

In certain embodiments, the first and second cells are substantially identical with the exception that the second cell contains an exogenous zinc finger protein and/or sequences encoding an exogenous zinc finger protein. In certain embodiments, there may be further genetic (and/or phenotypic) differences between the first and second cells.

In any of the methods described herein, the zinc finger protein can be a component of a fusion molecule, for example a fusion of a zinc finger protein and a functional domain. The functional domain may be, for example a repression domain such as KRAB, MBD-2B, v-ErbA, MBD3, unliganded TR, and members of the DNMT family; an activation domain such as VP16, the p65 subunit of NF-kappa B, ligand-bound TR, and VP64; an insulator domain; a chromatin remodeling protein or component of a chromatin remodeling complex; and/or a methyl binding domain. According to the methods, the zinc finger protein either activates or inhibits the expression of the target. The zinc finger protein (or fusion) can activate expression, for example, such that the expression level in the second cell is more than 125% or 175% of the expression level in the first cell. The zinc finger protein can inhibit expression, for example, such that the expression level in the second cell is less than 95%, 75%, 50%, 25% or 5% of the expression level in the first cell.

In certain embodiments, the molecular target is a protein. However, a molecular target is any molecule whose expression can be modulated by a zinc finger protein, for example, RNA, carbohydrate and/or lipid.

In any of the method described herein, the zinc finger protein (or fusion molecule) can be provided as a protein or as a polynucleotide encoding the protein or fusion molecule. Thus, according to the methods, the zinc finger protein is either expressed in, or added to, the second cell. In certain embodiments in which the zinc finger protein is provided as a polynucleotide, expression of the zinc finger protein can be inducible, for example using an inducible transcription control element (e.g., promoter) operably linked to the sequence encoding the zinc finger protein. In these embodiments, the first and second cells may both contain a polynucleotide encoding a zinc finger protein but expression is induced in only one of the two matched cells. Furthermore, the first and/or second cells may contain more than one exogenous zinc finger protein or fusion molecule (or polynucleotide encoding same).

In other aspects, the first and/or second cells used in the screening methods can also comprise a reporter (e.g., selectable marker). For example, in certain embodiments, methods are provided wherein a cell comprises a zinc finger protein whose expression is operably linked to a transcription control element responsive to a known molecular target, preferably a component of a cellular process such as a biochemical pathway or signal transduction pathway. Thus, under conditions in which the signal transduction pathway is active, the zinc finger protein is expressed. The cell also preferably comprises a polynucleotide encoding a reporter (e.g., a fluorescent protein, such as green fluorescent protein, a luciferase, a beta-galactosidase, a beta-glucuronidase, a beta-lactamase, a peroxidase such as horseradish peroxidase, an alkaline phosphatase, CAT, etc.). A subset of reporter molecules includes selectable markers (e.g., drug resistance, thymidine kinase, etc.). The reporter or selectable marker can be operably linked to transcriptional control elements that are modulated by the zinc finger protein (or fusion containing the zinc finger protein). Accordingly, when a test compound is administered to the cell, the ability of the compound to interact with a target (e.g., a component of a signal transduction pathway) to modulate production of the ZFP will be reflected in the amount of reporter and/or selectable marker produced. In certain embodiments, the zinc finger protein (or fusion) represses expression of the reporter and/or selectable marker. In these cases, if the compound interacts with its target in such a way as to block a signal transduction pathway, production of a reporter whose expression is controlled by the ZFP is increased. The cells may also comprise more than one reporter and/or selectable marker.

In additional embodiments, cells which overexpress a molecular target are provided, wherein overexpression is mediated by the action of an exogenous zinc finger protein. Similarly, cells which underexpress a molecular target, wherein underexpression is mediated by the action of an exogenous zinc finger protein, are provided. Methods of making and using such cells are also provided.

In still further embodiments, methods are provided that involve using one or more cellular components isolated from a cell containing an exogenous zinc finger protein. In preferred embodiments, the cellular component is cell membranes which are preferably isolated from cells that overexpress a molecular target (e.g., receptor) by virtue of the activity of the zinc finger protein (or fusion containing same). The isolated membranes can be used, for example, for binding studies (e.g., using radiolabeled ligands).

In another aspect, cells comprising any of the zinc finger proteins described herein are provided. In preferred embodiments, a cell that expresses a molecular target is provided. A cell of this sort exhibits a property that is responsive to the cell being contacted with a compound that interacts with the molecular target. The cell contains an exogenous zinc finger protein that modulates the production of a protein in the cell, preferably the molecular target.

In yet another aspect, kits for screening a compound of interest comprising any of the cells, proteins, polynucleotides and the like described herein are provided. In preferred embodiments, the kit further comprises ancillary reagents, instructions and other materials designed to carry out of the methods of screening described herein.

These and other embodiments will be readily apparent to the skilled artisan in view of the disclosure herein.

BRIEF DESCRIPTION OF THE DRAWINGS

FIG. 2, panels A–C depict inducible expression of the endogenous EPO gene in stably transformed 293 cells, in response to synthesis of a zinc finger protein (EPOZFP-862) under the control of a tetracycline responsive full-length CMV promoter.

DETAILED DESCRIPTION

Overview

Figure 1:
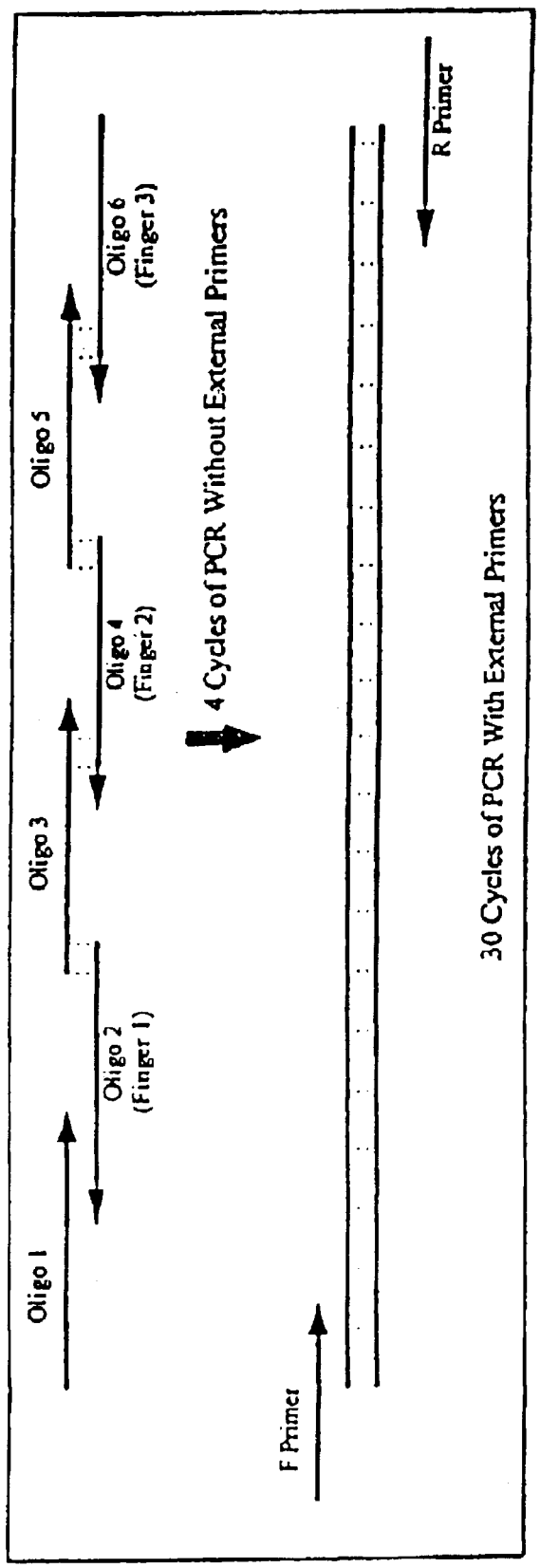
FIG. 1 shows the process of assembling a nucleic acid encoding a designed ZFP.

The compositions and methods disclosed herein include novel assays for screening candidate compounds for their ability to interact with particular molecular targets. The assays include both cell-based and biochemical assays. Furthermore, the assays described herein comprise or are derived from cells comprising a zinc finger protein that is capable of modulating expression of a gene of interest.

In one embodiment, zinc finger proteins or polynucleotides encoding these proteins are introduced into cells (e.g., via stable or transient transfection) to overexpress a molecular target of interest. The effect of a candidate compound on the molecular target in the ZFP-containing cells can be compared to the effect of the same compound in non-ZFP-containing cells to determine the ability of the compound to interact with the target. Thus, the ZFP can modulate (e.g., activate) expression of the molecular target itself. Alternatively, the ZFP can modulate expression of a different molecule which then acts directly or indirectly on the molecular target, for example the ZFP can modulate expression of an upstream or downstream molecule in a signal transduction pathway that modulates the molecular target.

In other embodiments, a gene encoding a ZFP is under the control of an inducible promoter and both first and second cells comprise the inducible gene. The cells are therefore substantially identical and expression of the ZFP can be induced in one cell (the test cell) and not in the other cell (the control cell) to determine the interaction of a candidate compound with the molecular target. The cells can be stably or transiently transfected with the inducible ZFP construct.

In another embodiment, zinc finger proteins are introduced into cells to overexpress a cell surface or membrane-bound molecule, for example a receptor. The receptor-rich membranes are then isolated and used for biochemical assays, for example by measuring binding of a compound.

In yet other embodiments, compounds are tested for their ability to interact with a molecular target, for example any target involved in a cellular process (e.g., a biochemical pathway or a signal transduction cascade). For example, a test compound is administered to a cell that is known to express a receptor that initiates a particular signal transduction cascade. Furthermore, the test cell also comprises (1) a polynucleotide encoding a fusion molecule comprising an exogenous zinc finger protein and a functional domain and (2) a polynucleotide encoding a reporter molecule (e.g., green fluorescent protein, or selectable marker such as drug resistance). The polynucleotide encoding the fusion molecule is operably linked to transcriptional control elements that are responsive to the cellular process of interest. For example, the polynucleotide encoding the fusion molecule can be operably linked to transcriptional control sequences derived from a gene whose expression is modulated as a result of the signal transduction cascade. The fusion molecule can comprise, for example, a zinc finger protein and a repression domain such that, when expressed, it represses expression of the reporter molecule. Thus, when the receptor and associated processes (e.g., signal transduction cascade) are functioning, the fusion molecule is expressed and, in turn, it serves to repress the expression of the reporter molecule. If a candidate test compound interacts with a component of the signal transduction pathway so as to block the pathway, expression of the repressive fusion molecule will be diminished or eliminated and the level of reporter will increase. Thus, any compound can be screened for its ability to interfere with a signal transduction cascade by monitoring reporter levels.

The practice of the disclosed methods employs, unless otherwise indicated, conventional techniques in molecular biology, biochemistry, genetics, computational chemistry, cell culture, recombinant DNA and related fields as are within the skill of the art.

These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The disclosures of all patents, patent applications and publications mentioned herein are hereby incorporated by reference in their entireties.

Definitions

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

A "zinc finger" is a sequence-specific binding domain comprising a polypeptide sequence (generally approximately 30 amino acids) having a structure that is stabilized by coordination of a zinc atom. A zinc finger can bind DNA, RNA and/or amino acid sequences. With respect to DNA binding, a single zinc finger generally binds to a target subsite comprising 2 to 4 base pairs, typically 3 or 4 base pairs. An exemplary class of zinc fingers has the general structure -Cys-$X_{2-4}$-Cys-$X_{12}$-His-$X_{3-5}$-His- (where X is any amino acid); comprising two cysteine residues and two histidine residues which coordinate the zinc atom (a so-called CCHH or $C_2H_2$ zinc finger). However, additional zinc finger structures such as, for example, CCHC, CCCH, CHHC, CHCH and CHHH are also useful in the disclosed methods and compositions.

A "zinc finger DNA binding protein" is a protein or segment within a larger protein that binds DNA in a sequence-specific manner through the binding activity of one or more zinc fingers. The term zinc finger DNA binding protein is often abbreviated as zinc finger protein or ZFP. A ZFP can comprise polypeptide domains in addition to zinc fingers; for example, other DNA-binding domains and/or functional domains.

A "designed" zinc finger protein is a protein not occurring in nature whose design/composition results principally from rational criteria. Rational criteria for design include application of substitution rules and computerized algorithms for processing information in a database storing information of existing ZFP designs and binding data, for example as described in co-owned PCT WO 00/42219.

A "selected" zinc finger protein is a protein not found in nature whose production results primarily from an empirical process such as phage display. See e.g., U.S. Pat. No. 5,789,538; U.S. Pat. No. 6,007,988; U.S. Pat. No. 6,013,453; WO 95/19431; WO 96/06166 and WO 98/54311.

An "optimized" zinc finger protein refers to a zinc finger protein which has been designed or selected as described supra, then tested for binding specificity and altered in sequence to improve its binding specificity, as described in co-owned International Publication WO 02/077227, published Oct. 3, 2002.

The term "naturally-occurring" is used to describe an object that can be found in nature, as distinct from being artificially produced by humans.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain. With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

"Specific binding" between, for example, a ZFP and a specific target site means a binding affinity of at least $1 \times 10^6$ $M^{-1}$.

A "regulatory domain" or "functional domain" refers to a polypeptide, protein or protein domain that has transcriptional modulation activity when tethered to a DNA binding domain, e.g., a ZFP. Typically, a regulatory domain is covalently or non-covalently linked to a ZFP (e.g., to form a fusion molecule) to effect transcription modulation. Regulatory domains can be activation domains or repression domains. Activation domains include, but are not limited to, VP16, VP64, ligand-bound wild-type thyroid hormone receptor (TR) and certain TR mutants, and the p65 subunit of nuclear factor Kappa-B. Repression domains include, but are not limited to, KRAB, MBD2B, unliganded wild-type TR and certain TR mutants, and v-ErbA. Additional regulatory domains include, e.g., transcription factors and co-factors (e.g., MAD, ERD, SID, early growth response factor 1, and nuclear hormone receptors), endonucleases, integrases, recombinases, methyltransferases, histone acetyltransferases, histone deacetylases etc. Activators and repressors include co-activators and co-repressors (see, e.g., Utley et al., Nature 394:498–502 (1998)). Alternatively, a ZFP can act alone, without a regulatory domain, to effect transcription modulation.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a methyl binding domain) and fusion nucleic acids (for example, a nucleic acid encoding the fusion polypeptide described herein). Examples of the second type of fusion molecule include, but are not limited to, a fusion between a triplex-forming nucleic acid and a polypeptide, and a fusion between a minor groove binder and a nucleic acid.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotien, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. For example, an exogenous nucleic acid can comprise a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include endogenous genes and endogenous proteins, for example, transcription factors and components of chromatin remodeling complexes.

A "gene," for the purposes of the present disclosure, includes a DNA region encoding a gene product (see below), as well as all DNA regions which regulate the production of the gene product, whether or not such regulatory sequences are adjacent to coding and/or transcribed sequences.

Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. A gene can be an endogenous cellular gene, either normal or mutant, or an exogenous gene of an infecting organism such as, for example, a bacterium or virus.

An "endogenous cellular gene" refers to a gene which is native to a cell, which is in its normal genomic and chromatin context, and which is not heterologous to the cell. Such cellular genes include, e.g., animal genes, plant genes, bacterial genes, protozoal genes fungal genes, mitochondrial genes and chloroplastic genes.

A "native chromatin context" refers to the naturally occurring, structural relationship of genomic DNA (e.g., bacterial, animal, fungal, plant, protozoal, mitochondrial, and chloroplastic) and DNA-binding proteins (e.g., histones, non-histone chromosomal proteins and bacterial DNA binding protein II), which together form chromosomes. An endogenous cellular gene can be in a transcriptionally active or inactive state in its native chromatin context.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process which results in an increase in production of a gene product. A gene product can be either RNA (including, but not limited to, mRNA, rRNA, tRNA, and structural RNA) or protein. Accordingly, gene activation includes those processes which increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

The term "modulate" refers to the suppression, enhancement or induction of a function. For example, a ZFP can modulate gene expression by binding to a motif within a transcriptional control sequence, thereby enhancing or suppressing transcription of a gene operatively linked to the transcriptional control sequence. Additionally, modulation includes inhibition of transcription of a gene by virtue of a ZFP binding to a gene and blocking DNA dependent RNA polymerase from reading through the gene, thus inhibiting transcription of the gene. Furthermore, modulation includes inhibition of translation of a transcript. Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, beta-glucuronidase, horseradish peroxidase, alkaline phosphatase, GFP (see, e.g., Mistili & Spector, (1997) *Nature Biotechnology* 15:961–964) or selectable markers such as drug resistance; changes in signal transduction; changes in phosphorylation and dephosphorylation; changes in receptor-ligand interactions; changes in concentrations of second messengers such as, for example, cGMP, cAMP, $IP_3$, and $Ca^{2+}$; changes in cell growth, changes in vascularization, and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, calorimetric reactions, antibody binding, inducible markers, ligand binding assays; changes in intracellular second messengers such as cGMP and inositol triphosphate ($IP_3$); changes in intracellular calcium levels; cytokine release, and the like.

When a zinc finger protein (or fusion molecule) is used to inhibit the expression of a cellular protein, the expression level of the cellular protein, and/or the mRNA encoding it, is preferably less than 75% of that in a reference cell that does not express or otherwise contain the zinc finger protein effecting regulation. Preferably, the expression level is less than 50% of that in the reference cell; more preferably it is less than 25% of that in the reference cell; most preferably it is less than 5% of that in the reference cell. When a zinc finger protein is used to activate the expression of a cellular protein, the expression level is more than 110% of that in a reference cell not expressing the ZFP. Preferably, the expression level is more than 125% of that in the reference cell; more preferably it is more than 150% of that in the original cell; most preferably it is more than 175% of that in the reference cell.

The terms "transcriptional control element," "transcriptional regulatory element," "transcriptional control sequence" and "transcriptional regulatory sequence" are used interchangeably to refer to DNA sequences which mediate modulation of transcription. Examples of such elements or sequences include, but are not limited to, promoters, operators, enhancers, silencers, splice donor and acceptor sites, transcription termination sites and polyadenylation sites. A transcriptional control sequence is responsive to a molecular target if the molecular target participates, either directly or indirectly, in modulation of transcription mediated by the control element.

"Eukaryotic cells" include, but are not limited to, fungal cells (such as yeast), protozoal cells, archael cells, plant cells, animal cells, mammalian cells and human cells. Similarly, "prokaryotic cells" include, but are not limited to, bacteria.

A "functional fragment" of a protein, polypeptide or nucleic acid is a protein, polypeptide or nucleic acid whose sequence is not identical to the full-length protein, polypeptide or nucleic acid, yet retains one or more functions exhibited by the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245–246; U.S. Pat. No. 5,585,245 and PCT WO 98/44350.

A "target site" or "target sequence" is a sequence that is bound by a binding protein such as, for example, a ZFP. Target sequences can be nucleotide sequences (either DNA or RNA) or amino acid sequences. By way of example, a DNA target sequence for a three-finger ZFP is generally either 9 or 10 nucleotides in length, depending upon the presence and/or nature of cross-strand interactions between the ZFP and the target sequence.

A "target subsite" or "subsite" is the portion of a DNA target site that is bound by a single zinc finger. Thus, in the absence of cross-strand interactions, a subsite is generally three nucleotides in length. In cases in which a cross-strand interaction occurs (e.g., a "D-able subsite" as described, for example, in co-owned PCT WO 00/42219, incorporated by reference in its entirety herein), a subsite is four nucleotides in length and overlaps with another 3- or 4-nucleotide subsite.

A "molecular target" refers to any molecule, for example a molecule within a cell or associated with a cell membrane, that is being examined for interaction with a candidate compound (e.g., a drug). Non-limiting examples of molecular targets include DNA, RNA and proteins such as receptors (e.g., cell surface, membrane-bound or nuclear), components of signal transduction pathways, transcription factors or functional fragments thereof. A molecular targets can also comprise a macromolecule such as a protein, nucleic acid, carbohydrate, lipid, glycoprotein, lipoprotien, polysaccharide, any modified derivative of the above molecules, or any complex comprising one or more of the above molecules. A compound "interacts" with a molecular target when it affects, directly or indirectly, the molecular target. The compound can act directly on the molecular target, for example when the molecular target is a protein, the compound may directly interact with the protein by binding to it or may directly regulate expression of the protein via action on transcriptional regulatory elements. Similarly, the compound may also act indirectly on the molecular target, for example by blocking or stimulating a separate molecule that in turn acts on the molecular target. Indirect action of a compound on a molecular target can occur, for example, when the target is a non-protein molecule and the compound interacts with a protein involved in the production, stability, activity, maintenance and/or modification of the non-protein molecular target.

The term "effective amount" includes that amount which results in the desired result, for example, deactivation of a previously activated gene or activation of an inactive gene, or that amount which results in the inactivation of a gene containing a zinc finger-nucleotide binding motif, or that amount which blocks transcription of a structural gene or translation of RNA.

"$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<$K_d$), as measured using a given assay system (see, e.g., U.S. Pat. No. 5,789,538). The assay system used to measure the $K_d$ should be chosen so that it gives the most accurate measure of the actual $K_d$ of the ZFP. Any assay system can be used, as long is it gives an accurate measurement of the actual $K_d$ of the ZFP. In one embodiment, the $K_d$ for the ZFPs is measured using an electrophoretic mobility shift assay ("EMSA"), as described in Example 1 of the present specification. Unless an adjustment is made for ZFP purity or activity, the $K_d$ calculations made using the method of Example 1 may result in an underestimate of the true $K_d$ of a given ZFP. Preferably, the $K_d$ of a ZFP used to modulate transcription of an endogenous cellular gene is less than about 100 nM, more preferably less than about 75 nM, more preferably less than about 50 nM, most preferably less than about 25 nM.

Screening Assays

In preferred embodiments, screening assays are conducted using cells comprising at least one exogenous zinc finger protein or using materials derived from cells comprising at least one exogenous zinc finger protein. The screening assays described herein allow for high throughput screening of candidate compounds, which can be accomplished while reducing the incidence of false positives.

A. Zinc Finger Proteins

The compositions and methods disclosed herein involve use of DNA binding proteins, particularly zinc finger proteins. See, for example, Miller et al. (1985) *EMBO J.* 4:1609–1614; Rhodes et al. (1993) *Scientific American* February:56–65; and Klug (1999) *J. Mol. Biol.* 293:215–218. The three-fingered Zif268 murine transcription factor has been particularly well studied. (Pavletich, N. P. & Pabo, C. O. (1991) *Science* 252:809–17). The X-ray co-crystal structure of Zif268 ZFP and double-stranded DNA indicates that each finger interacts independently with DNA (Nolte et al. (1998) *Proc Natl Acad Sci USA* 95:2938–43; Pavletich, N. P. & Pabo, C. O. (1993) *Science* 261:1701–7). The organization of the 3-fingered domain allows recognition of three contiguous base-pair triplets by each finger. Each finger is approximately 30 amino acids long, adopting a ββα fold. The two β-strands form a sheet, positioning the recognition α-helix in the major groove for DNA binding. Specific contacts with the bases are mediated primarily by four amino acids immediately preceding and within the recognition helix. Conventionally, these recognition residues are numbered −1, 2, 3, and 6 based on their positions in the α-helix.

ZFP DNA-binding domains are designed and/or selected to recognize a particular target site as described in co-owned WO 00/42219; WO 00/41566; WO 02/42459; as well as U.S. Pat. Nos. 5,789,538; 6,007,408; 6,013,453; 6,140,081; and 6,140,466; and PCT publications WO 95/19431, WO 98/54311, WO 00/23464 and WO 00/27878. In one embodiment, a target site for a zinc finger DNA-binding domain is identified according to site selection rules disclosed in co-owned WO 00/42219. In a preferred embodiment, a ZFP is selected as described in co-owned International Publication WO 02/077227. In certain preferred embodiments, the binding specificity of the DNA-binding domain can be determined by identifying accessible regions in the sequence in question (e.g., in cellular chromatin). Accessible regions can be determined as described in co-owned International Publications WO 01/83751 and WO 01/83732, both published Nov. 8, 2001, the disclosures of which are hereby incorporated by reference herein. A DNA-binding domain is then designed and/or selected as described herein to bind to a target site within the accessible region.

Two alternative methods are typically used to create the coding sequences required to express newly designed DNA-binding peptides. An example of one protocol is a PCR-based assembly procedure, for construction of a three-finger ZFP, that utilizes six overlapping oligonucleotides (see FIG. 1). Three oligonucleotides correspond to "universal" sequences that encode portions of the DNA-binding domain between the recognition helices. These oligonucleotides remain constant for all zinc finger constructs. The other three "specific" oligonucleotides are designed to encode the recognition helices. These oligonucleotides contain substitutions primarily at positions −1, 2, 3 and 6 on the recognition helices such that each specifies a distinct DNA-binding domain.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by a high-fidelity thermostable polymerase, the combination of Taq and Pfu polymerases also suffices. In the second phase of construction, the zinc finger template is amplified using external primers designed to incorporate restriction sites at both ends of the amplification product, to facilitate its cloning into a shuttle vector or directly into an expression vector.

An alternative method of assembling a sequence to encode a designed DNA-binding protein relies on annealing complementary oligonucleotides encoding the specific regions of the desired zinc finger protein. This particular application requires that the oligonucleotides be phosphorylated prior to the final ligation step. This is usually performed before setting up the annealing reactions, but phosphorylation (e.g., by polynucleotide kinase) can also occur post-annealing. In brief, the "universal" oligonucleotides encoding the constant regions of the proteins are annealed to complementary oligonucleotides. Additionally, the "specific" oligonucleotides encoding the finger recognition helices are annealed with their respective complementary oligonucleotides. These complementary oligos are designed to fill in the region, which was previously filled in by polymerase in the protocol described above. Oligonucleotides complementary to universal oligo 1 and specific oligo 6 (encoding finger 3) are engineered to contain overhanging sequences specific for the restriction sites used in cloning into the vector of choice. The second assembly protocol differs from the initial protocol in the following aspects: the "scaffold" encoding the newly designed zinc finger protein is composed entirely of synthetic DNA, thereby eliminating the polymerase fill-in step, additionally the fragment to be cloned into the vector does not require amplification. Lastly, the inclusion of sequence-specific overhangs eliminates the need for restriction enzyme digestion prior to insertion into a vector.

The resulting fragment encoding the newly designed zinc finger protein is ligated into an expression vector. Expression vectors that are commonly utilized include, but are not limited to, a modified pMAL-c2 bacterial expression vector (New England BioLabs, "NEB," Beverly, Mass.) or a eukaryotic expression vector, pcDNA (Promega, Madison, Wis.). Conventional methods of purification can be used (see Ausubel, supra, Sambrook, supra). In addition, any suitable host can be used, e.g., bacterial cells, insect cells, yeast cells, mammalian cells, and the like.

Expression of the zinc finger protein fused to a maltose binding protein (MBP-ZFP) in bacterial strain JM109 allows for straightforward purification through an amylose column (NEB). High expression levels of the zinc finger chimeric protein can be obtained by induction with IPTG since the MBP-ZFP fusion in the pMal-c2 expression plasmid is under the control of the IPTG inducible tac promoter (NEB). Bacteria containing the MBP-ZFP fusion plasmids are inoculated in to 2×YT medium containing 10 $\mu$M $ZnCl_2$, 0.02% glucose, plus 50 $\mu$g/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 μM $ZnCl_2$, then eluted with maltose in essentially the same buffer (purification is based on a standard protocol from NEB). Purified proteins are quantitated and stored for biochemical analysis.

The biochemical properties of the purified proteins, e.g., $K_d$, can be characterized by any suitable assay. $K_d$ can be characterized via electrophoretic mobility shift assays ("EMSA") (Buratowski & Chodosh, in *Current Protocols in Molecular Biology* pp. 12.2.1–12.2.7 (Ausubel ed., 1996); see also U.S. Pat. No. 5,789,538; PCT WO 00/42219, hereby incorporated by reference). Affinity is measured by titrating purified protein against a low fixed amount of labeled double-stranded oligonucleotide target. The target comprises the natural binding site sequence (9 or 18 bp) flanked by the 3 bp found in the natural sequence. External to the binding site plus flanking sequence is a constant sequence. The annealed oligonucleotide targets possess a 1 bp 5' overhang which allows for efficient labeling of the target with T4 phage polynucleotide kinase. For the assay the target is added at a concentration of 40 nM or lower (the actual concentration is kept at least 10-fold lower than the lowest protein dilution) and the reaction is allowed to equilibrate for at least 45 min. In addition the reaction mixture also contains 10 mM Tris (pH 7.5), 100 mM KCl, 1 mM $MgCl_2$, 0.1 mM $ZnCl_2$, 5 mM DTT, 10% glycerol, 0.02% BSA (poly (dIdC) or (dAdT) (Pharmacia) can also added at 10–100 μg/μl).

The equilibrated reactions are loaded onto a 10% polyacrylamide gel, which has been pre-run for 45 min in Tris/glycine buffer, then bound and unbound labeled target is resolved be electrophoresis at 150V (alternatively, 10–20% gradient Tris-HCl gels, containing a 4% polyacrylamide stacker, can be used). The dried gels are visualized by autoradiography or phosphoroimaging and the apparent $K_d$ is determined by calculating the protein concentration that gives half-maximal binding.

Similar assays can also include determining active fractions in the protein preparations. Active fractions are determined by stoichiometric gel shifts where proteins are titrated against a high concentration of target DNA. Titrations are done at 100, 50, and 25% of target (usually at micromolar levels).

B. Fusion Molecules

The selection and/or design of zinc finger-containing proteins also allows for the design of fusion molecules which facilitate regulation of gene expression. Thus, in certain embodiments, the compositions and methods disclosed herein involve fusions between a zinc finger protein (or functional fragment thereof) and one or more functional domains (or functional fragments thereof), or a polynucleotide encoding such a fusion. When such a fusion molecule is present in a cell, a functional domain is brought into proximity With a sequence in a gene that is bound by the zinc finger protein. The transcriptional regulatory function of the functional domain is then able to act on the gene, by, for example, modulating expression of the gene.

The zinc finger protein can be covalently or non-covalently associated with one or more regulatory domains, alternatively two or more regulatory domains, with the two or more domains being two copies of the same domain, or two different domains. The regulatory domains can be covalently linked to the zinc finger protein, e.g., via an amino acid linker, as part of a fusion protein. The zinc finger proteins can also be associated with a regulatory domain via a non-covalent dimerization domain, e.g., a leucine zipper, a STAT protein N terminal domain, or an FK506 binding protein (see, e.g., O'Shea, *Science* 254: 539 (1991), Barahmand-Pour et al., *Curr. Top. Microbiol. Immunol.* 211:121–128 (1996); Klemm et al., *Annu. Rev. Immunol.* 16:569–592 (1998); Klemm et al., *Annu. Rev. Immunol.* 16:569–592 (1998); Ho et al., *Nature* 382:822–826 (1996); and Pomeranz et al., *Biochem.* 37:965 (1998)). The regulatory domain can be associated with the zinc finger protein at any suitable position, including the C- or N-terminus of the zinc finger protein.

Common regulatory domains for addition to the zinc finger protein include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos and/or erb family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include, for example, transcription factors, their effector domains, coactivators, silencers, and nuclear hormone receptors. See, e.g., Goodrich et al, *Cell* 84:825–30 (1996) for a review of proteins and nucleic acid elements involved in transcription; transcription factors in general are reviewed in Barnes & Adcock, *Clin. Exp. Allergy* 25 Suppl. 2:46–9 (1995) and Roeder, *Methods Enzymol.* 273:165–71 (1996). Databases dedicated to transcription factors are known (see, e.g., *Science* 269:630 (1995)). Nuclear hormone receptor transcription factors are described in, for example, Rosen et al, *J. Med. Chem.* 38:4855–74 (1995). The C/EBP family of transcription factors are reviewed in Wedel et al., *Immunobiology* 193:171–85 (1995). Coactivators and co-repressors that mediate transcription regulation by nuclear hormone receptors are reviewed in, for example, Meier, *Eur. J. Endocrinol.* 134(2):158–9 (1996); Kaiser et al, *Trends Biochem. Sci.* 21:342–5 (1996); and Utley et al., *Nature* 394:498–502 (1998)). GATA transcription factors, which are involved in regulation of hematopoiesis, are described in, for example, Simon, *Nat. Genet.* 11:9–11 (1995); Weiss et al., *Exp. Hematol.* 23:99–107. TATA box binding protein (TBP) and its associated TAF polypeptides (which include TAF30, TAF55, TAF80, TAF110, TAF150, and TAF250) are described in Goodrich & Tjian, *Curr. Opin. Cell Biol.* 6:403–9 (1994) and Hurley, *Curr. Opin. Struct. Biol.* 6:69–75 (1996). The STAT family of transcription factors is reviewed in, for example, Barahmand-Pour et al., *Curr. Top. Microbiol. Immunol.* 211:121–8 (1996). Transcription factors involved in disease are reviewed in Aso et al., *J. Clin. Invest.* 97:1561–9 (1996).

An exemplary functional domain for fusing with a ZFP is a KRAB repression domain from the human KOX-1 protein (see, e.g., Thiesen et al., New Biologist 2, 363-374 (1990); Margolin et al., Proc. Natl. Acad. Sci. USA 91, 4509–4513 (1994); Pengue et al., Nucl. Acids Res. 22:2908–2914 (1994); Witzgall et al., Proc. Natl. Acad. Sci. USA 91, 4514–4518 (1994). Another suitable repression domain is methyl binding domain protein 2B (MBD-2B) (see, also Hendrich et al. (1999) *Mamm Genome* 10:906–912 for description of MBD proteins). Another useful repression domain is that associated with the v-ErbA protein. See, for example, Damm, et al. (1989) *Nature* 339:593–597; Evans (1989) *Int. J. Cancer Suppl.* 4:26–28; Pain et al. (1990) *New Biol.* 2:284–294; Sap et al. (1989) *Nature* 340:242–244; Zenke et al. (1988) *Cell* 52:107–119; and Zenke et al. (1990) *Cell* 61:1035–1049. Additional exemplary repression domains include, but are not limited to, unliganded (e.g., not bound to T3) thyroid hormone receptor (TR) and certain TR mutants, SID, MBD2, MBD3, members of the DNMT family (e.g., DNMT1, DNMT3A, DNMT3B), Rb, and MeCP2. See, for example, Zhang et al. (2000); *Ann Rev Physiol* 62:439–466; Bird et al. (1999) *Cell* 99:451–454; Tyler et al. (1999) *Cell* 99:443–446; Knoepfler et al. (1999) *Cell* 99:447–450; and Robertson et al. (2000) *Nature Genet.* 25:338–342. Additional exemplary repression domains include, but are not limited to, ROM2 and AtHD2A. See, for example, Chern et al. (1996) *Plant Cell* 8:305–321; and Wu et al. (2000) *Plant J.* 22:19–27.

Suitable domains for achieving activation include the HSV VP 16 activation domain (see, e.g., Hagmann et al., J. Virol. 71, 5952–5962 (1997)) nuclear hormone receptors (see, e.g., Torchia et al., Curr. Opin. Cell. Biol. 10:373–383 (1998)); ligand-bound TR and certain TR mutants; the p65 subunit of nuclear factor kappa B (Bitko & Barik, J. Virol. 72:5610–5618 (1998) and Doyle & Hunt, Neuroreport 8:2937–2942 (1997)); Liu et al., Cancer Gene Ther. 5:3–28 (1998)), or artificial chimeric functional domains such as VP64 (Seifpal et al., EMBO J. 11, 4961–4968 (1992)).

Additional exemplary activation domains include, but are not limited to, p300, CBP, PCAF, SRC1 PvALF, AtHD2A and ERF-2. See, for example, Robyr et al. (2000) *Mol. Endocrinol.* 14:329–347; Collingwood et al. (1999) *J. Mol. Endocrinol.* 23:255–275; Leo et al. (2000) *Gene* 245:1–11; Manteuffel-Cymborowska (1999) *Acta Biochim. Pol.* 46:77–89; McKenna et al. (1999) *J. Steroid Biochem. Mol. Biol.* 69:3–12; Malik et al. (2000) *Trends Biochem. Sci.* 25:277–283; and Lemon et al. (1999) *Curr. Opin. Genet. Dev.* 9:499–504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21–29; Okanami et al. (1996) *Genes Cells* 1:87–99; Goff et al. (1991) *Genes Dev.* 5:298–309; Cho et al. (1999) *Plant Mol. Biol.* 40:419–429; Ulmason et al. (1999) *Proc. Natl. Acad. Sci. USA* 96:5844–5849; Sprenger-Haussels et al. (2000) *Plant J.* 22:1–8; Gong et al. (1999) *Plant Mol. Biol.* 41:33–44; and Hobo et al. (1999) *Proc. Natl. Acad. Sci. USA* 96:15,348–15,353.

Additional functional domains are disclosed, for example, in co-owned WO 00/41566. Further, insulator domains, chromatin remodeling proteins such as ISWI-containing domains and/or methyl binding domain proteins suitable for use in fusion molecules are described, for example, in co-owned International Publications WO 02/26959, published Apr. 4, 2002; WO 02/44376, published Jun. 6, 2002; and WO 02/26960, published Apr. 4, 2002.

Functional domains can also be derived from nuclear hormone receptors. For example, the thyroid hormone receptor (TR) is a member of the nuclear hormone receptor superfamily and is normally bound constitutively to its target genes. The effect of TR binding (i.e., either repression or activation of gene expression) ordinarily depends upon the presence or absence of its ligand, thyroid hormone (T3). In the absence of T3 the receptor generally represses gene expression to a level below the basal level. A number of proteins have been identified that are recruited by the unliganded receptor and are believed to constitute a repressive complex. Examples of such proteins include SMRT and NCoR, which interact directly with the receptor, as well as Sin3, which interacts with SMRT/NCoR. Sin3 also interacts with a number of histone deacetylases, for example, HDACs 1 through 8 (some of which may also interact directly with TR). Recruitment of histone deacetylases by DNA-bound TR is believed to play a major role in its ability to confer repression; however, it is also possible that repressive factors other than HDACs are recruited by TR.

Binding of ligand to DNA-bound TR results in the decay of the repressive complex associated with the TR and recruitment of activating factors to the DNA-bound, ligand-bound TR. Such activating factors include, but are not limited to, the histone acetyltransferases SRC-1, CBP/p300 and P/CAF. Oligomeric activation complexes can also be recruited by ligand-bound TR, such as, for example, DRIP and ARC. Rachez et al. (1999) *Nature* 398:824–827; and Naar et al. (1999) *Nature* 398:828–832. These have been shown to interact with other nuclear hormone receptors, in response to ligand binding, and facilitate activation of gene expression in the context of a chromatin template. Another member of the nuclear receptor family, the glucocorticoid receptor (GR), recruits the hBRG1/BAF chromatin remodeling complex in response to ligand binding. Fryer et al. (1998) *Nature* 393:88–91.

TR and related nuclear receptors are modular proteins comprising an amino-terminal region (of undefined function), a central DNA binding domain and a carboxy-terminal ligand binding domain (LBD). The LBD, in addition to binding hormone, is responsible for interactions with both the repressive and activating factors described above. When the LBD is fused to a heterologous DNA binding domain (Gal4), it mediates repression of a target promoter containing a Gal4 binding site. Collingwood et al. (1998) *EMBO J.* 17:4760–4770. In addition, T3-dependent activation of transcription can be achieved using a fusion of the TR LBD with the Gal4 DNA-binding domain. Tone et al. (1994) *J. Biol. Chem.* 269:31,157–31,161.

Knowledge of the structure of the LBD of TR and related nuclear receptors, together with the results of mutagenesis studies, can be used to design mutant receptors whose repression and activation activity are impervious to hormone concentration. For example, single amino acid mutants of TR that are unable to bind physiological levels of T3 (e.g. G344E, Δ430M, and Δ276I) recruit corepressors to their binding site. Collingwood et al. (1994) *Mol. Endocrinol.* 8:1262–1277; Collingwood et al. (1998) supra. Conversely, mutations causing conformational changes in the ligand binding domain that mimic those induced by hormone binding have been identified in the estrogen receptor (e.g. L536P and Y541D/E/A) and generate constitutively activating forms of the receptor. Eng et al. (1997) *Mol. Cell. Biol.* 17:4644–4653; White et al. (1997) *EMBO J.* 16:1427–1435.

Accordingly, a mutant nuclear hormone receptor LBD derived, for example, from TR or GR can be used as a component of a fusion with a ZFP DNA-binding domain, to recruit activating or repressing protein complexes to a region of interest in cellular chromatin, thereby regulating expression of a target molecule. Certain naturally-occurring mutant LBDs are available; and new mutants can be constructed by methods well-known to those of skill in the art. The site of action of such complexes is determined by the specificity of the DNA-binding domain; while their activity is determined by the nature of the mutation to the LBD and is independent of ligand concentration. For instance, a fusion comprising a LBD that has been mutated such that it is unable to bind hormone will facilitate formation of repressive complexes;

while a fusion molecule comprising a LBD mutation that changes the conformation of the LBD such that it resembles a ligand-bound LBD will stimulate the formation of complexes that facilitate transcriptional activation. Thus, for the purposes of the present disclosure, a mutant nuclear hormone receptor LBD (such as TR) can be used as an activation or repression domain.

In additional embodiments, targeted remodeling of chromatin, as disclosed in co-owned U.S. patent application entitled "Targeted Modification of Chromatin Structure," can be used to generate one or more sites in cellular chromatin that are accessible to the binding of a functional domain/DNA binding domain fusion molecule.

Kinases, phosphatases, and other proteins that modify polypeptides involved in gene regulation are also useful as functional domains for zinc finger proteins. Such modifiers are often involved in switching on or off transcription mediated by, for example, hormones. Kinases involved in transcription regulation are reviewed in Davis, *Mol. Reprod. Dev.* 42:459–67 (1995), Jackson et al., *Adv. Second Messenger Phosphoprotein Res.* 28:279–86 (1993), and Boulikas, *Crit. Rev. Eukaryot. Gene Expr.* 5:1–77 (1995), while phosphatases are reviewed in, for example, Schonthal & Semin, *Cancer Biol.* 6:239–48 (1995). Nuclear tyrosine kinases are described in Wang, *Trends Biochem. Sci.* 19:373–6 (1994).

Useful domains can also be obtained from the gene products of oncogenes (e.g., myc, jun, fos, myb, max, mad, rel, ets, bcl, myb, mos and/or erb family members) and their associated factors and modifiers. Oncogenes are described in, for example, Cooper, *Oncogenes, The Jones and Bartlett Series in Biology* (2$^{nd}$ ed., 1995). The ets transcription factors are reviewed in Waslylk et al., *Eur. J. Biochem.* 211:7–18 (1993) and Crepieux et al., *Crit. Rev. Oncog.* 5:615–38 (1994). Myc oncogenes are reviewed in, for example, Ryan et al., *Biochem. J.* 314:713–21 (1996). The jun and fos transcription factors are described in, for example, *The Fos and Jun Families of Transcription Factors* (Angel & Herrlich, eds. 1994). The max oncogene is reviewed in Hurlin et al., *Cold Spring Harb. Symp. Quant. Biol.* 59:109–16. The myb gene family is reviewed in Kanei-Ishii et al., *Curr. Top. Microbiol. Immunol.* 211:89–98 (1996). The mos family is reviewed in Yew et al., *Curr. Opin. Genet. Dev.* 3:19–25 (1993).

Zinc finger proteins can include functional domains obtained from DNA repair enzymes and their associated factors and modifiers. DNA repair systems are reviewed in, for example, Vos, *Curr. Opin. Cell Biol.* 4:385–95 (1992); Sancar, *Ann. Rev. Genet.* 29:69–105 (1995); Lehmann, *Genet. Eng.* 17:1–19 (1995); and Wood, *Ann. Rev. Biochem.* 65:135–67 (1996). DNA rearrangement enzymes and their associated factors and modifiers can also be used as regulatory domains (see, e.g., Gangloff et al., *Experientia* 50:261–9 (1994); Sadowski, *FASEB J.* 7:760–7 (1993)).

Similarly, regulatory domains can be derived, from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays,* 16:13–22 (1994), and methyltransferases are described in Cheng, *Curr. Opin. Struct. Biol.* 5:4–10 (1995). Chromatin associated proteins and their modifiers (e.g., kinases, acetylases and deacetylases), such as histone deacetylase (Wolffe, *Science* 272:371–2 (1996)) are also useful as domains for addition to the zinc finger protein of choice. A DNA methyl transferase that acts as a transcriptional repressor can also be the regulatory domain. (see, e.g., Van den Wyngaert et al., *FEBS Lett.* 426:283–289 (1998); Flynn et al., *J. Mol. Biol.* 279:101–116 (1998); Okano et al., *Nucleic Acids Res.* 26:2536–2540 (1998); and Zardo & Caiafa, *J. Biol. Chem.* 273:16517–16520 (1998)). Endonucleases such as FokI can also be used as transcriptional repressors, which act via gene cleavage (see, e.g., WO95/09233; and PCT/US94/01201).

Factors that control chromatin and DNA structure, movement and localization and their associated factors and modifiers; factors derived from microbes (e.g., prokaryotes, eukaryotes and virus) and factors that associate with or modify them can also be used to obtain fusion proteins. Recombinases and integrases can be used as functional domains. Histone acetyltransferase can also be used as a transcriptional activator (see, e.g., Jin & Scotto, *Mol. Cell. Biol.* 18:4377–4384 (1998); Wolffe, *Science* 272:371–372 (1996); Taunton et al., *Science* 272:408–411 (1996); and Hassig et al., *Proc. Natl. Acad. Sci. U.S.A.* 95:3519–3524 (1998)). Histone deacetylase can be used as a transcriptional repressor (see, e.g., Jin & Scotto, *Mol. Cell. Biol.* 18:4377–4384 (1998); Syntichaki & Thireos, *J. Biol. Chem.* 273:24414–24419 (1998); Sakaguchi et al., *Genes Dev.* 12:2831–2841 (1998); and Martinez et al., *J. Biol. Chem.* 273:23781–23785 (1998)).

Linker domains between polypeptide domains, e.g., between two zinc finger proteins or between a zinc finger protein and a functional domain, can be included. Such linkers are typically polypeptide sequences, such as poly gly sequences of between about 5 and 200 amino acids. Preferred linkers are typically flexible amino acid subsequences which are synthesized as part of a recombinant fusion protein. For example, the linker DGGGS (SEQ ID NO: 28) can be used to link two zinc finger proteins. The flexible linker linking two zinc finger proteins can also be an amino acid subsequence comprising the sequence TGEKP (SEQ ID NO: 29) (see, e.g., Liu et al., *Proc. Natl. Acad. Sci. U.S.A.* 5525–5530 (1997)). The linker LRQKDGERP (SEQ ID NO: 30) can be used to link two zinc finger proteins. The following linkers can also be used to link two zinc finger proteins: GGRR (SEQ ID NO: 31) (Pomerantz et al. 1995, supra), (G4S)$_n$ (SEQ ID NO: 45) (Kim et al., *Proc. Natl. Acad. Sci. U.S.A.* 93, 1156–1160 (1996.); and GGRRGGGS (SEQ ID NO: 32); LRQRDGERP (SEQ ID NO: 33); LRQKDGGGSERP (SEQ ID NO: 34); LRQKd(G3S)$_2$ ERP (SEQ ID NO: 35). Alternatively, flexible linkers can be rationally designed using computer program capable of modeling both DNA-binding sites and the peptides themselves (Desjarlais & Berg, *Proc. Natl. Acad. Sci. U.S.A.* 90:2256–2260(1993), *Proc. Natl. Acad. Sci. U.S.A.* 91:11099–11103 (1994) or by phage display methods (e.g., PCT WO 99/45132).

A chemical linker can be used to connect synthetically or recombinantly produced domain sequences. For example, poly(ethylene glycol) linkers are available from Shearwater Polymers, Inc. Huntsville, Ala. Some linkers have amide linkages, sulfhydryl linkages, or heterofunctional linkages. In addition to covalent linkage of zinc finger proteins to regulatory domains, non-covalent methods can be used to produce molecules with zinc finger proteins associated with regulatory domains.

ZFP fusion molecules can also comprise, in addition to or instead of one or more functional domains, one or more domains that facilitate purification, expression monitoring and/or determination of cellular and/or subcellular localization. These include, for example, polypeptides such as maltose binding protein ("MBP"), glutathione S transferase (GST), hexahistidine, c-myc, and the FLAG epitope.

Fusion molecules are constructed by methods of cloning and biochemical conjugation that are well-known to those of skill in the art. In certain embodiments, fusion molecules comprise a zinc finger protein and at least two functional domains (e.g., an insulator domain or a methyl binding protein domain and, additionally, a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

The fusion molecules disclosed herein comprise a zinc finger binding protein which binds to a target site and modulates expression of a molecular target. In certain embodiments, the target site is present in an accessible region of cellular chromatin. Accessible regions can be determined as described in co-owned International Publications WO 01/83751 and WO 01/83732, both published Nov. 8, 2001. If the target site is not present in an accessible region of cellular chromatin, one or more accessible regions can be generated as described in co-owned International Publication WO 01/83793, published Nov. 8, 2001. In additional embodiments, the zinc finger component of a fusion molecule is capable of binding to cellular chromatin regardless of whether its target site is in an accessible region or not. For example, such DNA binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261–270; Pina et al. (1990) *Cell* 60:719–731; and Cirillo et al. (1998) EMBO J. 17:244–254.

Methods of gene regulation using one or more functional domains, targeted to a specific sequence by virtue of a fused DNA binding domain, can achieve modulation of gene expression. Modulation of gene expression can be in the form of decreased expression (e.g., repression). In this case, the value of a cellular property in a cell in which expression of a molecular target is repressed by a ZFP is often lower than the value of that property in a cell not expressing a repressive ZFP directed to the molecular target. As described herein, repression of a specific target gene can be achieved by using a fusion molecule comprising a zinc finger protein and a functional domain.

Alternatively, modulation can be in the form of increased gene expression, or activation, if activation of a gene encoding the molecular target is required to test interaction of a compound with a molecular target. The functional domain (e.g., insulator domain, activation domain, etc.) enables increased and/or sustained expression of the target gene. The value of a cellular property in a cell in which expression of a molecular target is increased by a ZFP is often greater than the value of that property in a cell not expressing an activating ZFP directed to the molecular target.

Some cells are designed to express a sequence encoding a zinc finger protein in operable linkage to an inducible promoter. A variety of inducible promoters are available; many of which can be regulated by small molecules or other environmental factors such as, for example, temperature and nutritional conditions. Operable linkage to an inducible promoter allows activation of a ZFP, and thereby modulation of expression of a molecular target by the ZFP, to be controlled by supplying the cell with the appropriate small molecule or inducing stimulus. Regulation of expression of ZFPs by inducible promoters is useful for achieving transient modulation of expression of a molecular target whose permanent over- or under-expression would result in lethality to the cell. Inducible expression is also advantageous in reducing secondary effects due to modulation of a molecular target. For example, modulation of expression of one cellular protein can directly or indirectly result in changes in the relative abundance of many others proteins (and other molecules) within the cell. By inducing expression of a zinc finger protein shortly before an assay is performed, such secondary changes are minimized. Accordingly, differences in response between a test cell, comprising a regulated molecular target, and a control cell, are entirely or substantially entirely due to interaction between the compound and the molecular target rather than to secondary effects caused by regulation of the target.

C. Cell-Based Assays

In one aspect, methods of performing cell-based drug-screening assays that reduce the incidence of false positives common to other conventional methods are described. False positives occur, for example, when a compound does not interact with an endogenous target but achieves the same or similar effect through an alternative mechanism.

In the present methods, false positives are reduced or eliminated by performing assays on matched populations of cells that preferably differ only in the expression level of at least one molecular target (e.g., a protein target or a protein that modulates the expression of the molecular target). Typically, a control population of cells expresses a molecular target at levels that are normal for the particular cell type and environmental (e.g., culture) conditions. A test population of cells expresses a molecular target at altered levels (either higher or lower) compared to the control population. Altered levels of expression of the molecular target are achieved by a ZFP or a ZFP fusion molecule which acts to modulate expression of the target molecule. Expression of the target molecule can be modulated directly as, for example, when a ZFP or a ZFP fusion molecule regulates transcription of a gene encoding the molecular target. Alternatively, indirect modulation of expression of a target molecule occurs when a ZFP or ZFP fusion molecule regulates expression of a gene that is involved in the synthesis, stability or regulation of the target molecule. Indirect modulation can occur in cases in which the molecular target is not a protein; although indirect modulation of a protein molecular target is also possible.

In one embodiment, a molecular target is overexpressed in the test cells. A compound is screened in the test cell population for its ability to interact with the overexpressed molecular target, for example using one or more assays that measure (quantitatively or qualitatively) interaction with the molecular target. The same compound is also screened in the control population and its ability to interact with the molecular target is also determined using the assays used in the test cell population. If a compound elicits a similar response in these two populations of cells, it is likely that the compound is not exerting its effect through an interaction with the molecular target. Conversely, if a compound elicits different responses in these two populations of cells, it is likely that the compound is interacting with the molecular target (e.g., directly or indirectly). Generally, if a molecular target is overexpressed in a test cell, the magnitude of the response is greater in the test cell than in the control cell. Thus, if a compound suspected of interacting with the target exerts a greater effect on the test cell than on the control cell, the compound likely exerts its effect through the intended target. However, in certain cases, the magnitude of a response can be smaller in a test cell that is overexpressing a molecular target, for example, if the molecular target represses a cellular component involved in the response.

In certain embodiments, the test and control cells differ in that the test cell does not express, or expresses at reduced levels, a molecular target for drug screening that is expressed in the control cell. If a compound suspected of interacting with the target exerts a similar effect on the control and test cells, then the compound is not exerting its effect through the intended molecular target interaction. For test cells which expresses a molecular target at levels lower than those at which it is expressed in a control cell, a compound that interacts with the molecular target will generally have a smaller effect in the test cells than in the control cells.

In other embodiments, the test and control cells differ in that the control cell does not express or expresses at reduced levels a protein that is structurally similar to a molecular target and that can transduce a similar cellular response to that resulting from transduction through the molecular target. If a compound suspected of interacting with the target exerts a different effect on the control and test cells, then the compound is not exerting its effect through the intended molecular target interaction.

Test cells are preferably generated by regulation of cellular genes with zinc finger proteins or fusion molecules described herein. In some methods, a test cell is produced by engineering a cell to express an exogenous zinc finger protein (or fusion molecule) designed to repress expression of an endogenous molecular target. In alternative methods, a test cell is produced by engineering a cell to express an exogenous zinc finger protein (or fusion molecule) designed to activate or increase expression of an endogenous molecular target. The resulting test cells are preferably substantially identical to the corresponding control cells except for an exogenous nucleic acid encoding the exogenous zinc finger-containing molecule (and, possibly, a low incidence of random mutations resulting from environmental factors). Thus, in certain embodiments, the phenotype of the test and controls cell populations will differ only in regard to the levels of the protein(s) subject to regulation by the exogenous zinc finger-containing molecule (and other secondary changes resulting from regulation of that protein). In other embodiments, the test and control cells may not be substantially identical but, in these cases, the genetic differences (besides any exogenous ZFP-coding polynucleotides) are typically known.

Control cells and test cells used in the present methods can be individual cells or cell populations, the latter being more usual. The cell types can be cell lines or natural (e.g., isolated) cells such as, for example, primary cells. Cell lines are available, for example from the American Type Culture Collection (ATCC), or can be generated by methods known in the art, as described for example in Freshney et al., *Culture of Animal Cells, A Manual of Basic Technique*, 3rd ed., 1994, and references cited therein. Similarly cells can be isolated by methods known in the art. Other non-limiting examples of cell types include cells that have or are subject to pathologies, such as cancerous cells and transformed cells, pathogenically infected cells, stem cells, fully differentiated cells, partially differentiated cells, immortalized cells and the like. Both prokaryotic (e.g., bacterial) and eukaryotic (e.g., yeast, plant, fungal, piscine and mammalian cells such as feline, canine, murine, bovine, porcine and human) cells can be used, with eukaryotic cells being preferred. Mammalian (human and non-human) cell types are particularly preferred. Archaeal cells can also be used.

The choice of cell type depends in part on the intended recipient of the drug being tested. For example, human cell types are advantageous for screening drugs intended for use in human, and feline cell types are advantageous for screening drugs intended for use in cats.

Suitable mammalian cell lines include CHO (chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1–977) J. Gen. Virol. 36:59), and myeloma cells like SP2 or NS0 (see, e.g., Galfre and Milstein (1981) Meth. Enzymol. 73(B):3–46. Other eukaryotic cells include, for example, insect (e.g., sp. *frugiperda*), fungal cells, including yeast (e.g., *S. cerevisiae, S. pombe, P. pastoris, K. lactis, H. polymorpha*), and plant cells (Fleer, R. (1992) Current Opinion in Biotechnology 3:486–496). Bacterial cell types include *E. coli, B. subtilis* and *S. typhimurium*.

The cells can be transiently or stably transfected or transformed with the ZFP or fusion molecule (or polynucleotide encoding the ZFP or fusion molecule). Methods of transfecting cells are known in the art and described for example in Ausubel et al., supra. Example 11 shows how 293 cells can be stably transfected with a nucleic acid molecule encoding a ZFP that activates erythropoietin (EPO) expression.

Furthermore, as noted above, zinc finger proteins can be designed to suppress or activate expression of essentially any cellular gene. Accordingly, ZFPs and ZFP fusions can be designed to repress expression of a protein that is structurally related to an intended molecular target or to overexpress a molecular target, to generate cells suitable for cell-based HTS assays.

One can use a number of methods in applying zinc finger-containing cells to cell-based assays for drug discovery. The test cell population and the control cell population, for example, can be put in two different vessels. A solution of a candidate compound can be added sequentially to both vessels and a cellular property for each cell population quantified and/or observed. When there is a significant difference (i.e., outside the scope of experimental error) between values of the cellular property for the respective cell populations, one determines the candidate compound to be a "hit" in the assay.

Another method involves first contacting the control cell population with a candidate compound and measuring a particular cellular response. The value of the response serves as a baseline measure for the assay. One then contacts the test cell population with the candidate compound and measures the same cellular response. A statistically different value for the two responses indicates that the compound is a "hit"; it substantially interacts with the molecular target. This method can also be done in the opposite order, where one first assays the test cell population.

In other methods, zinc finger proteins are used to enhance expression of a molecular target in a test cell. Such test cells can optionally be used in conjunction with control cells in which the target is expressed at normal levels or other test cells in which the target is expressed at subnormal levels. Alternatively, test cells in which expression of a molecular target is enhanced can be used without comparison to control cells. For example, one can perform an analysis in which cellular response is measured in the presence and absence of a compound.

In some methods, analysis of cellular response in test and control cells is performed in parallel. In other methods, analysis of cellular response in test cells is compared with historical controls. In some methods, cellular response in the presence of a compound in either test or control cells is compared with the response of like cells in absence of the compound.

Virtually any component of a cell can serve as a molecular target for drug screening. Typically, the molecular target is a polypeptide. Non-limiting examples of molecular targets of interest include growth factor receptors (e.g., FGFR, PDGFR, EFG, NGFR, and VEGF). Other targets are G-protein receptors and include substance K receptor, the angiotensin receptor, the α- and β-adrenergic receptors, the serotonin receptors, and PAF receptor. See, e.g., Gilman, *Ann. Rev. Biochem.* 56:625–649 (1987). Other targets include ion channels (e.g., calcium, sodium, potassium channels), muscannic receptors, acetylcholine receptors, GABA receptors, glutamate receptors, and dopamine receptors (see Harpold, U.S. Pat. No. 5,401,629 and U.S. Pat. No. 5,436,128). Other targets are adhesion proteins such as integrins, selecting, and immunoglobulin superfamily members (see Springer, *Nature* 346:425–433 (1990). Osborn, *Cell* 62:3 (1990); Hynes, *Cell* 69:11 (1992)). Other targets are cytokines, such as interleukins IL-1 through IL-13, tumor necrosis factors α & β interferons α, β and γ, transforming growth factor Beta (TGF-β), colony stimulating factor (CSF) and granulocyte/macrophage colony stimulating factor (GM-CSF). See Human Cytokines: Handbook for Basic & Clinical Research (Aggrawal et al. eds., Blackwell Scientific, Boston, Mass. 1991). Other targets are hormones, enzymes, and intracellular and intercellular messengers, such as, adenyl cyclase, guanyl cyclase, and phospholipase C, nuclear receptors (e.g., FXR (Farnesoid X Receptor), PPARs (Peroxisome Proliferator Activator Receptors), and RZR (Retinoid Z Receptor)), and organelle receptors. Target molecules can be human, mammalian viral, plant, fungal or bacterial. Other targets are antigens, such as proteins, glycoproteins and carbohydrates from microbial pathogens, both viral and bacterial, and tumors. Still other targets are described in U.S. Pat. No. 4,366,241. Some compound screened for interaction with a target merely bind to a target. Other compounds agonize or antagonize the target.

In some methods, compounds are screened individually. In other methods, many compounds are screened in parallel. Microtiter plates and robotics are particularly useful for parallel screening of many compounds. Optical detection is also preferred for rapidity and automation. Hundreds, thousands or even millions of compounds can be screened per week.

Once a "hit" is identified using the present methods derivatives of the compound can be made to maximize its ability to interact with the molecular target. Derivatives can be produced using conventional techniques such as self-consistent field (SCF) analysis, configuration interaction (CI) analysis, and normal mode dynamics analysis. Computer programs for implementing these techniques are readily available. See Rein et al., *Computer-Assisted Modeling of Receptor-Ligand Interactions* (Alan Liss, New York, 1989). Compound derivatives are subjected to rescreening in the cell-based assay to select the one(s) that demonstrate the best interaction profile with the molecular target.

In other embodiments, the cells are engineered such that a reporter system is operably linked to signal transduction through a molecular target. Reporter expression can be directly detected by detecting formation of transcript or of translation product. For example, transcription product can be detected using RNA (Northern) blots and the formation of certain proteins can be detected using a characteristic stain or by detecting an inherent characteristic of the protein. More typically, however, expression of reporter is determined by detecting a product formed as a consequence of an activity of the reporter.

Thus, cell based screening assays can be performed in which ZFPs mediate a positive response (e.g., activation of a reporter and/or selectable marker) to a negative signal, for example release of a reporter or selectable marker from ZFP-controlled repression as a result of blockage of an event in a signal transduction cascade. For instance, to screen a compound for its effect on a known signal transduction cascade, the compound is administered to a cell that is known to express a target that is involved in a particular signal transduction cascade. In certain embodiments, the target is a cell surface or membrane-bound receptor so that the compound does not need to traverse the cell membrane or wall. In other embodiments, the target is an intracellular component of the signal transduction cascade and, accordingly, the compound can be also be administered directly into the cell using methods known in the art and described herein.

Typically, in these positive-response assays, the test cell comprises (1) a polynucleotide encoding a fusion molecule comprising an exogenous zinc finger protein and a functional domain (e.g., a repression domain) and (2) a polynucleotide encoding a reporter and/or selectable molecule (e.g., green fluorescent protein, drug resistance, etc.). The polynucleotide encoding the fusion molecule is operably linked to transcriptional control elements responsive to the signal transduction cascade of interest. In embodiments in which the functional domain is a repression domain, the fusion molecule is designed such that, when expressed, it represses expression of the reporter molecule. Thus, when the signal transduction cascade is functioning, the fusion molecule is expressed and, in turn, it serves to repress the expression of the reporter molecule. If a test compound interferes with expression of the repressive fusion molecule, for example by blocking a component of the signal transduction pathway that acts, directly or indirectly, on the control elements which regulate transcription of the fusion molecule, repression of reporter molecule expression is diminished and increased levels of reporter expression are observed. Thus, any compound can be screened for its ability to interfere with a signal transduction cascade by monitoring reporter levels or using positive and/or negative selections to monitor modulation of the reporter (e.g., selectable marker) molecule by the ZFP.

Any of the methods described herein can be used with any reporter and/or selectable marker. Reporters that can be directly detected include fluorescent molecules such as, for example, GFP (green fluorescent protein). Fluorescence is detected using a variety of commercially available fluorescent detection systems, including a fluorescence-activated cell sorter (FACS) system for example. Other reporters are enzymes that catalyze the formation of a detectable product. Suitable enzymes include proteases, nucleases, lipases, phosphatases, sugar hydrolases and esterases. Examples of suitable reporter genes that encode enzymes include, for example, CAT (chloramphenicol acetyl transferase; Alton and Vapnek (1979) Nature 282:864–869), luciferase, β-galactosidase, β-glucuronidase, β-lactamase, horseradish peroxidase and alkaline phosphatase (e.g., Toh, et al. (1980) Eur. J. Biochem. 182:231–238; and Hall et al. (1983) J. Mol. Appl. Gen. 2:101).

Selectable markers form a subset or reporter molecules and can also be used instead of, or in addition to, the directly detectable reporters described above. Positive selection markers are those polynucleotides that encode a product that enables only cells that carry and express the gene to survive and/or grow under certain conditions. For example, cells that express neomycin resistance (Neo$^r$) gene are resistant to the compound G418, while cells that do not express Neo$^r$ are skilled by G418. Other examples of positive selection markers including hygromycin resistance, Zeocin® resistance and the like will be known to those of skill in the art. Negative selection markers are those polynucleotides that encode a produce that enables only cells that carry and express the gene to be killed under certain conditions. For example, cells that express thymidine kinase (e.g., herpes simplex virus thymidine kinase, HSV-TK) are killed when gancyclovir is added. Other negative selection markers are known to those skilled in the art. The selectable marker need not be a transgene and, additionally, reporters and selectable markers can be used in various combinations.

D. Biochemical Assays

Also described herein are methods of performing biochemical drug-screening assays. An important biochemical assay to test for drugs that affect a specific receptor involves isolation of cell membranes comprising the receptor of interest and testing for binding of candidate compounds. Thus, cells that overexpress particular proteins associated with cell membranes (e.g., receptors) can be readily generated using zinc finger proteins that activate expression of these proteins. Subsequently, the membranes of the cells that overexpress the protein of interest can be readily isolated for use in assays, for example binding assays.

E. Compounds and Cell Properties

The methods described herein are useful in screening a wide variety of compounds. For example, compounds to be screened in the present methods can be from combinatorial libraries of peptides or small molecules, hormones, growth factors, and cytokines, can be naturally occurring molecules, or can be from existing repertoires of chemical compounds synthesized by the pharmaceutical industry. Combinatorial libraries can be produced for many types of compound that can be synthesized in a step-by-step fashion. Such compounds include, for example, polypeptides, beta-turn mimetics, polysaccharides, nucleic acids, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. Compounds to be screened can also be obtained from the National Cancer Institute's Natural Product Repository, Bethesda, Md. Existing compounds or drugs with known efficacy can also be screened to evaluate side effects and/or additional indications.

Furthermore, a variety of cellular and/or biochemical responses (also termed cell properties) can be measured and compared in the methods described herein. In some methods, the value of the cell property is measured as a function of cell growth, neovascularization, hormone release, pH changes, changes in intracellular second messengers such as GMP, binding to receptor and the like.

In other embodiments, the cellular response to administration of a compound is normally quantified as a value of a cellular property. The units of the value depend on the property. For example, the units can be units of absorbance, photon count, radioactive particle count or optical density.

Delivery of Molecules

When the molecular target is intracellular, a compound that interacts with it must traverse the cell membrane. A compound contacted with a cell can cross the cell membrane in a number of ways. If the compound has suitable size and charge properties, it can be passively transported across the membrane. Other processes of membrane passage include active transport (e.g., receptor mediated transport), endocytosis and pinocytosis. Where a compound cannot be effectively transported by any of the preceding methods, microinjection, biolistics or other methods can be used to deliver it to the internal portion of the cell. Alternatively, if the compound to be screened is a protein, a nucleic acid encoding the protein can be introduced into the cell and expressed within the cell.

Likewise, the exogenous zinc finger protein that effects regulation within a cell must be introduced into the cell. Typically such is achieved by introducing either the ZFP molecule or a nucleic acid encoding the ZFP into the cell resulting in expression of the zinc finger protein within the cell. Nucleic acids can be introduced by conventional means including viral based methods, chemical methods, lipofection and microinjection. The introduced nucleic acid can integrate into the host chromosome, persist in episomal form or can have a transient existence in the cytoplasm. Similarly, an exogenous protein can be introduced into a cell in protein form. For example, the zinc finger protein can be introduce by lipofection, biolistics, or microinjection or through fusion to membrane translocating domains.

Thus, the compositions described herein can be provided to the target cell in vitro or in vivo. In addition, the compositions can be provided as polypeptides, polynucleotides or combination thereof.

A. Delivery of Polynucleotides

In certain embodiments, the compositions are provided as one or more polynucleotides. Further, as noted above, a zinc finger protein-containing composition can be designed as a fusion between a polypeptide zinc finger and a functional domain, that is encoded by a fusion nucleic acid. In both fusion and non-fusion cases, the nucleic acid can be cloned into intermediate vectors for transformation into prokaryotic or eukaryotic cells for replication and/or expression. Intermediate vectors for storage or manipulation of the nucleic acid or production of protein can be prokaryotic vectors, (e.g., plasmids), shuttle vectors, insect vectors, or viral vectors for example. A nucleic acid encoding a zinc finger protein can also cloned into an expression vector, for administration to a bacterial cells, fungal cells, protozoal cells, plant cells, or animal cells such as piscine cells or mammalian cells, preferably a human cell.

To obtain expression of a cloned nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, *Gene Transfer and Expression: A Laboratory Manual* (1990). Bacterial expression systems are available in, e.g., *E. coli, Bacillus* sp., and *Salmonella*. Palva et al. (1983) *Gene* 22:229–235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

The promoter used to direct expression of the nucleic acid of choice depends on the particular application. For example, a strong constitutive promoter is typically used for expression and purification. In contrast, when a protein is to be used in vivo, either a constitutive or an inducible promoter is used, depending on the particular use of the protein. In addition, a weak promoter can be used, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system. See, e.g., Gossen et al. (1992) *Proc. Natl. Acad. Sci USA* 89:5547–5551; Oligino et al. (1998) *Gene Ther.* 5:491–496; Wang et al. (1997) *Gene Ther.* 4:432–441; Neering et al. (1996) *Blood* 88:1147–1155; and Rendahl et al. (1998) *Nat. Biotechnol.* 16:757–761.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the nucleic acid sequence, and signals required, e.g., for efficient polyadenylation of the transcript, transcriptional termination, ribosome binding, and/or translation termination. Additional elements of the cassette may include, e.g., enhancers, and heterologous spliced intronic signals.

The particular expression vector used to transport the genetic information into the cell is selected with regard to the intended use of the resulting ZFP polypeptide, e.g., expression in plants, animals, bacteria, fungi, protozoa etc. Standard bacterial expression vectors include plasmids such as pBR322, pBR322-based plasmids, pSKF, pET23D, and commercially available fusion expression systems such as GST and LacZ. Epitope tags can also be added to recombinant proteins to provide convenient methods of isolation, for monitoring expression, and for monitoring cellular and subcellular localization, e.g., c-myc or FLAG.

Regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rou's sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High-yield expression systems are also suitable, such as baculovirus vectors in insect cells, with a nucleic acid sequence coding for a ZFP as described herein under the transcriptional control of the polyhedrin promoter or any other strong baculovirus promoter.

Elements that are typically included in expression vectors also include a replicon that functions in *E. coli* (or in the prokaryotic host, if other than *E. coli*), a selective marker, e.g., a gene encoding antibiotic resistance, to permit selection of bacteria that harbor recombinant plasmids, and unique restriction sites in nonessential regions of the vector to allow insertion of recombinant sequences.

Standard transfection methods can be used to produce bacterial, mammalian, yeast, insect, or other cell lines that express large quantities of zinc finger proteins, which can be purified, if desired, using standard techniques. See, e.g., Colley et al. (1989) *J. Biol. Chem.* 264:17619–17622; and *Guide to Protein Purification, in Methods in Enzymology*, vol. 182 (Deutscher, ed.) 1990. Transformation of eukaryotic and prokaryotic cells are performed according to standard techniques. See, e.g., Morrison (1977) *J. Bacteriol.* 132:349–351; Clark-Curtiss et al. (1983) in *Methods in Enzymology* 101:347–362 (Wu et al., eds).

Any procedure for introducing foreign nucleotide sequences into host cells can be used. These include, but are not limited to, the use of calcium phosphate transfection, DEAE-dextran-mediated transfection, polybrene, protoplast fusion, electroporation, lipid-mediated delivery (e.g., liposomes), microinjection, particle bombardment, introduction of naked DNA, plasmid vectors, viral vectors (both episomal and integrative) and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Conventional viral and non-viral based nucleic acid delivery methods can be used to introduce nucleic acids into host cells or target tissues. Such methods can be used to administer nucleic acids to cells in vitro. Additionally, nucleic acids are administered in vivo or ex vivo. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For reviews of nucleic acid delivery procedures, see, for example, Anderson (1992) *Science* 256:808–813; Nabel et al. (1993) *Trends Biotechnol.* 11:211–217; Mitani et al. (1993) *Trends Biotechnol.* 11:162–166; Dillon (1993) *Trends Biotechnol.* 11:167–175; Miller (1992) *Nature* 357:455–460; Van Brunt (1988) *Biotechnology* 6(10):1149–1154; Vigne (1995) *Restorative Neurology and Neuroscience* 8:35–36; Kremer et al. (1995) *British Medical Bulletin* 51(1):31–44; Haddada et al., in *Current Topics in Microbiology and Immunology*, Doerfler and Böhm (eds), 1995; and Yu et al. (1994) *Gene Therapy* 1: 13–26.

Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386; 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Nucleic acid can be delivered to cells (in vitro or ex vivo administration) or to target tissues (in vivo administration).

The preparation of lipid:nucleic acid complexes, including targeted liposomes such as immunolipid complexes, is well known to those of skill in the art. See, e.g. Crystal (1995) *Science* 270:404–410; Blaese et al. (1995) *Cancer Gene Ther.* 2:291–297; Behr et al. (1994) *Bioconjugate Chem.* 5:382–389; Remy et al. (1994) *Bioconjugate Chem.* 5:647–654; Gao et al. (1995) *Gene Therapy* 2:710–722; Ahmad et al. (1992) *Cancer Res.* 52:4817–4820; and U.S. Pat. Nos. 4,186,183; 4,217,344; 4,235,871; 4,261,975; 4,485,054; 4,501,728; 4,774,085; 4,837,028 and 4,946,787.

The use of RNA or DNA virus-based systems for the delivery of nucleic acids take advantage of highly evolved processes for targeting a virus to specific cells in the body and trafficking the viral payload to the nucleus. Viral vectors can be administered directly to subjects (in vivo) or they can be used to treat cells in vitro or ex vivo. Conventional viral based systems for the delivery of ZFPs include retroviral, lentiviral, poxyiral, adenoviral, adeno-associated viral, vesicular stomatitis viral and herpesviral vectors. Integration in the host genome is possible with certain viral vectors, including the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, allowing alteration and/or expansion of the potential target cell population. Lentiviral vectors are retroviral vector that are able to transduce or infect non-dividing cells and typically produce high viral titers. Selection of a retroviral nucleic acid delivery system would therefore depend on the target cell and/or tissue. Retroviral vectors have a packaging capacity of up to 6–10 kb of foreign sequence and are comprised of cis-acting long terminal repeats (LTRs). The minimum cis-acting LTRs are sufficient for replication and packaging of the vectors, which are then used to integrate the exogenous gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof. Buchscher et al. (1992) *J. Virol.* 66:2731–2739; Johann et al. (1992) *J. Virol.* 66:1635–1640; Sommerfelt et al. (1990) *Virol.* 176:58–59; Wilson et al. (1989) *J. Virol.* 63:2374–2378; Miller et al. (1991) *J. Virol.* 65:2220–2224; and PCT/US94/05700). pLASN and MFG-S are examples of retroviral vectors that have been used in clinical trials. Dunbar et al. (1995) *Blood* 85:3048–305; Kohn et al. (1995) *Nature Med.* 1:1017–102; Malech et al. (1997) *Proc. Natl. Acad. Sci. USA* 94:12133–12138. PA317/pLASN was the first therapeutic vector used in a gene therapy trial. (Blaese et al. (1995) *Science* 270:475–480. Transduction efficiencies of 50% or greater have been observed for MFG-S packaged vectors. Ellem et al. (1997) *Immunol Immunother.* 44(1):10–20; Dranoff et al. (1997) *Hum. Gene Ther.* 1:111–2.

Adeno-associated virus (AAV) vectors are also used to transduce cells with target nucleic acids, e.g., in the in vitro production of nucleic acids and peptides, and for in vivo and ex vivo applications. See, e.g., West et al. (1987) *Virology* 160:38–47; U.S. Pat. No. 4,797,368; WO 93/24641; Kotin (1994) *Hum. Gene Ther.* 5:793–801; and Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251–3260; Tratschin, et al. (1984) *Mol. Cell. Biol.* 4:2072–2081; Hermonat et al. (1984) *Proc. Natl. Acad. Sci. USA* 81:6466–6470; and Samulski et al. (1989) *J. Virol.* 63:3822–3828.

Recombinant adeno-associated virus vectors based on the defective and nonpathogenic parvovirus adeno-associated virus type 2 (AAV-2) are a promising nucleic acid delivery system. Exemplary AAV vectors are derived from a plasmid containing the AAV 145 bp inverted terminal repeats flanking a transgene expression cassette. Efficient transfer of nucleic acids and stable transgene delivery due to integration into the genomes of the transduced cell are key features for this vector system. Wagner et al. (1998) *Lancet* 351 (9117):1702–3; and Kearns et al. (1996) *Gene Ther.* 9:748–755.

In applications for which transient expression is preferred, adenoviral-based systems are useful. Adenoviral based vectors are capable of very high transduction efficiency in many cell types and are capable of infecting, and hence delivering nucleic acid to, both dividing and non-dividing cells. With such vectors, high titers and levels of expression have been obtained. Adenovirus vectors can be produced in large quantities in a relatively simple system.

Replication-deficient recombinant adenovirus (Ad) vectors can be produced at high titer and they readily infect a number of different cell types. Most adenovirus vectors are engineered such that a transgene replaces the Ad E1a, E1b, and/or E3 genes; the replication defector vector is propagated in human 293 cells that supply the required E1 functions in trans. Ad vectors can transduce multiple types of tissues in vivo, including non-dividing, differentiated cells such as those found in the liver, kidney and muscle. Conventional Ad vectors have a large carrying capacity for inserted DNA. An example of the use of an Ad vector in a clinical trial involved polynucleotide therapy for antitumor immunization with intramuscular injection. Sterman et al. (1998) *Hum. Gene Ther.* 7:1083–1089. Additional examples of the use of adenovirus vectors for nucleic acid delivery include Rosenecker et al. (1996) *Infection* 24:5–10; Sterman et al., supra; Welsh et al. (1995) *Hum. Gene Ther.* 2:205–218; Alvarez et al. (1997) *Hum. Gene Ther.* 5:597–613; and Topf et al. (1998) *Gene Ther.* 5:507–513.

Packaging cells are used to form virus particles that are capable of infecting a host cell. Such cells include 293 cells, which package adenovirus, and Ψ2 cells or PA317 cells, which package retroviruses. Viral vectors used in nucleic acid delivery are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. Missing viral functions are supplied in trans, if necessary, by the packaging cell line. For example, AAV vectors used in nucleic acid delivery typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment, which preferentially inactivates adenoviruses.

In many nucleic acid delivery applications, it is desirable that the vector be delivered with a high degree of specificity to a particular tissue type. A viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747–9751 reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., $F_{ab}$ or $F_v$) having specific binding affinity for virtually any chosen cellular receptor. Although the above description applies primarily to viral vectors, the same principles can be applied to non-viral vectors. Such vectors can be engineered to contain specific uptake sequences thought to favor uptake by specific target cells.

Vectors can be delivered in vivo by administration to a subject, typically by systemic administration (e.g., intravenous, intraperitoneal, intramuscular, subdermal, or intracranial infusion) or topical application, as described infra. Alternatively, vectors can be delivered to cells in vitro or ex vivo, such as cells explanted from a subject (e.g., lymphocytes, bone marrow aspirates, tissue biopsy).

In one embodiment, hematopoietic stem cells are used in in vitro procedures for cell transfection and nucleic acid delivery. The advantage to using stem cells is that they can be differentiated into other cell types in vitro. Methods for differentiating CD34+ stem cells in vitro into clinically important immune cell types using cytokines such a GM-CSF, IFN-γ and TNF-α are known. Inaba et al. (1992) *J. Exp. Med.* 176:1693–1702.

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells). See Inaba et al., supra.

B. Delivery of Polypeptides

In other embodiments, ZFPs or ZFP fusion proteins are administered directly to target cells. In certain in vitro situations, the target cells are cultured in a medium containing one or more fusion proteins comprising functional domains fused to one or more of the ZFPs.

An important factor in the administration of polypeptide compounds is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins, lipids and other compounds, which have the ability to translocate polypeptides across a cell membrane, have been described.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58. Prochiantz (1996) *Curr. Opin. Neurobiol.* 6:629–634. Another subsequence, the h (hydrophobic) domain of signal peptides, was found to have similar cell membrane translocation characteristics. Lin et al. (1995) *J. Biol. Chem.* 270:14255–14258.

Examples of peptide sequences which can be linked to a zinc finger polypeptide (or fusion containing the same) for facilitating its uptake into cells include, but are not limited to: an 11 amino acid peptide of the tat protein of HIV; a 20 residue peptide sequence which corresponds to amino acids 84–103 of the p16 protein (see Fahraeus et al. (1996) *Curr. Biol.* 6:84); the third helix of the 60-amino acid long homeodomain of Antennapedia (Derossi et al. (1994) *J. Biol. Chem.* 269:10444); the h region of a signal peptide, such as the Kaposi fibroblast growth factor (K-FGF) h region (Lin et al., supra); and the VP22 translocation domain from HSV (Elliot et al. (1997) *Cell* 88:223–233). Other suitable chemical moieties that provide enhanced cellular uptake can also be linked, either covalently or non-covalently, to the ZFPs.

Toxin molecules also have the ability to transport polypeptides across cell membranes. Often, such molecules (called "binary toxins") are composed of at least two parts: a translocation or binding domain and a separate toxin domain. Typically, the translocation domain, which can optionally be a polypeptide, binds to a cellular receptor, facilitating transport of the toxin into the cell. Several bacterial toxins, including *Clostridium perfringens* iota toxin, diphtheria toxin (DT), Pseudomonas exotoxin A (PE), pertussis toxin (PT), *Bacillus anthracis* toxin, and pertussis adenylate cyclase (CYA), have been used to deliver peptides to the cell cytosol as internal or amino-terminal fusions. Arora et al. (1993) *J. Biol. Chem.* 268:3334–3341; Perelle et al. (1993) *Infect. Immun.* 61:5147–5156; Stenmark et al. (1991) *J. Cell Biol.* 113:1025–1032; Donnelly et al. (1993) *Proc. Natl. Acad. Sci. USA* 90:3530–3534; Carbonetti et al. (1995) *Abstr. Annu. Meet. Am. Soc. Microbiol.* 95:295; Sebo et al. (1995) *Infect. Immun.* 63:3851–3857; Klimpel et al. (1992) *Proc. Natl. Acad. Sci. USA.* 89:10277–10281; and Novak et al. (1992) *J. Biol. Chem.* 267:17186–17193.

Such subsequences can be used to translocate polypeptides, including the polypeptides as disclosed herein, across a cell membrane. This is accomplished, for example, by derivatizing the fusion polypeptide with one of these translocation sequences, or by forming an additional fusion of the translocation sequence with the fusion polypeptide. Optionally, a linker can be used to link the fusion polypeptide and the translocation sequence. Any suitable linker can be used, e.g., a peptide linker.

A suitable polypeptide can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the molecule(s) to be delivered to the cell.

The liposome fuses with the plasma membrane, thereby releasing the molecule(s) into the cytosol. Alternatively, the liposome is phagocytosed or taken up by the cell in a transport vesicle. Once in the endosome or phagosome, the liposome is either degraded or it fuses with the membrane of the transport vesicle and releases its contents.

In current methods of drug delivery via liposomes, the liposome ultimately becomes permeable and releases the encapsulated molecule(s) at the target tissue or cell. For systemic or tissue specific delivery, this can be accomplished, for example, in a passive manner wherein the liposome bilayer is degraded over time through the action of various agents in the body. Alternatively, active drug release involves using an agent to induce a permeability change in the liposome vesicle. Liposome membranes can be constructed so that they become destabilized when the environment becomes acidic near the liposome membrane. See, e.g., *Proc. Natl. Acad. Sci. USA* 84:7851 (1987); *Biochemistry* 28:908 (1989). When liposomes are endocytosed by a target cell, for example, they become destabilized and release their contents. This destabilization is termed fusogenesis. Dioleoylphosphatidylethanolamine (DOPE) is the basis of many "fusogenic" systems.

For use with the methods and compositions disclosed herein, liposomes typically comprise a fusion polypeptide as disclosed herein, a lipid component, e.g., a neutral and/or cationic lipid, and optionally include a receptor-recognition molecule such as an antibody that binds to a predetermined cell surface receptor or ligand (e.g., an antigen). A variety of methods are available for preparing liposomes as described in, e.g.; U.S. Pat. Nos. 4,186,183; 4,217,344; 4,235,871; 4,261,975; 4,485,054; 4,501,728; 4,774,085; 4,837,028; 4,235,871; 4,261,975; 4,485,054; 4,501,728; 4,774,085; 4,837,028; 4,946,787; PCT Publication No. WO 91/17424; Szoka et al. (1980) *Ann. Rev. Biophys. Bioeng.* 9:467; Deamer et al. (1976) *Biochim. Biophys. Acta* 443:629–634; Fraley, et al. (1979) *Proc. Natl. Acad. Sci. USA* 76:3348–3352; Hope et al. (1985) *Biochim. Biophys. Acta* 812:55–65; Mayer et al. (1986) *Biochim. Biophys. Acta* 858:161–168; Williams et al. (1988) *Proc. Natl. Acad. Sci. USA* 85:242–246; Liposomes, Ostro (ed.), 1983, Chapter 1); Hope et al. (1986) *Chem. Phys. Lip.* 40:89; Gregoriadis, *Liposome Technology* (1984) and Lasic, *Liposomes: from Physics to Applications* (1993). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it may be desirable to target a liposome using targeting moieties that are specific to a particular cell type, tissue, and the like. Targeting of liposomes using a variety of targeting moieties (e.g., ligands, receptors, and monoclonal antibodies) has been previously described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumor cells can also be targeted by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Virally infected cells can be targeted using various viral antigens such as hepatitis B core and surface antigens (HBVc, HBVs) hepatitis C antigens, Epstein-Barr virus antigens, human immunodeficiency type-1 virus (HIV-1) and papilloma virus antigens. Inflammed cells can be targeted using molecules specifically recognized by surface molecules which are expressed at sites of inflammation such as integrins (e.g., VCAM-1), selectin receptors (e.g., ELAM-1) and the like.

Standard methods for coupling targeting agents to liposomes are used. These methods generally involve the incorporation into liposomes of lipid components, e.g., phosphatidylethanolamine, which can be activated for attachment of targeting agents, or incorporation of derivatized lipophilic compounds, such as lipid derivatized bleomycin. Antibody targeted liposomes can be constructed using, for instance, liposomes which incorporate protein A. See Renneisen et al. (1990) *J. Biol. Chem.* 265:16337–16342 and Leonetti et al. (1990) *Proc. Natl. Acad. Sci. USA* 87:2448–2451.

Kits

Also provided are kits for performing any of the above methods. The kits typically contain cells for use in the above methods or components for making such cells. For example, some kits contain pairs of test and control cells differing in that one cell population is transformed with an exogenous nucleic acid encoding a zinc finger protein designed to regulate expression of a molecular target (e.g., a protein) within the test cells. Some kits contain a single cell type and other components that allow one to produce test cells from that cell type. Such components can include a vector encoding a zinc finger protein or the zinc finger protein itself. The kits can also contain necessary containers, buffers for transformation of cells, culture media for cells, and/or buffers for performing assays. Typically, the kits also contain a label indicating that the cells are to be used for screening compounds. A label includes any material such as instructions, packaging or advertising leaflet that is attached to or otherwise accompanies the other components of the kit.

EXAMPLES

The following examples are offered to illustrate, but are not in any way intended to be limiting.

Example 1

This first Example demonstrates the construction of ZFPs designed to recognize DNA sequences contained in the promoter of the human vascular endothelial growth factor (VEGF) gene. VEGF is an approximately 46 kDa glycoprotein that is an endothelial cell-specific mitogen induced by hypoxia. VEGF has been implicated in angiogenesis associated with cancer, various retinopathies, and other serious diseases. The DNA target site chosen was a region surrounding the transcription initiation site of the gene. The two 9 base pair (bp) sites chosen are found within the sequence agcGGGGAGGAT̲cGCGGAGGCTtgg (SEQ ID NO:1), where the upper-case letters represent actual 9-bp targets. The protein targeting the upstream 9-bp target was denoted VEGF1, and the protein targeting the downstream 9-bp target was denoted VEGF3a. The major start site of transcription for VEGF is at the T at the 3' end of the first 9-bp target, which is underlined in the sequence above.

The human SP-1 transcription factor was used as a progenitor molecule for the construction of designed ZFPs. SP-1 has a three finger DNA-binding domain related to the well-studied murine Zif268 (Christy et al., *PNAS* 85:7857–7861 (1988)). Site-directed mutagenesis experiments using this domain have shown that the proposed "recognition rules" that operate in Zif268 can be used to adapt SP-1 to other target DNA sequences (Desjarlais & Berg, *PNAS* 91:11099–11103 (1994)). The SP-1 sequence used for construction of zinc finger clones corresponds to amino acids 533 to 624 in the SP-1 transcription factor.

The selection of amino acids in the recognition helices of the two designed ZFPs, VEGF1 and VEGF3a, is summarized in Table 1.

TABLE 1

Amino acids chosen for recognition helices of VEGF-recognizing ZFPs

| Position: | Finger 1 | | | | Finger 2 | | | | Finger 3 | | | |
|---|---|---|---|---|---|---|---|---|---|---|---|---|
| Protein | −1 | 2 | 3 | 6 | −1 | 2 | 3 | 6 | −1 | 2 | 3 | 6 |
| VEGF1 | T | S | N | R | R | S | N | R | R | D | H | R |
| VEGF3A | Q | S | D | R | R | S | N | R | R | D | E | R |

Coding sequences were constructed to express these peptides using a PCR-based assembly procedure that utilizes six overlapping oligonucleotides. Three oligonucleotides corresponding to "universal" sequences that encode portions of the DNA-binding domain between the recognition helices. These oligonucleotides remain constant for any zinc finger construct. Three "specific" oligonucleotides were designed to encode the recognition helices. These oligonucleotides contained substitutions at positions −1, 2, 3 and 6 on the recognition helices to make them specific for each of the different DNA-binding domains. Codon bias was chosen to allow expression in both mammalian cells and *E. coli*.

The PCR synthesis was carried out in two steps. First, the double stranded DNA template was created by combining the six oligonucleotides (three universal, three specific) and using a four cycle PCR reaction with a low temperature (25° C.) annealing step. At this temperature, the six oligonucleotides join to form a DNA "scaffold." The gaps in the scaffold were filled in by a combination of Taq and Pfu polymerases. In the second phase of construction, the zinc finger template was amplified in thirty cycles by external primers that were designed to incorporate restriction sites for cloning into pUC19. Accuracy of clones for the VEGF ZFPs were verified by DNA sequencing. The DNA sequences of each of the two constructs are listed below.

HCl (pH 8.0), 100 μM $ZnCl_2$, 5 mM DTT. The samples were boiled for 10 min. and centrifuged for 10 min. at ~3,000×g. At this point the ZFP protein in the supernatant was >50% pure as estimated by staining of SDS polyacrylamide gels with Coomassie blue, and the product migrated at the predicted molecular weight of around 11 kDa.

The second method of producing ZFPs was to express them as fusions to the *E. coli* Maltose Binding Protein (MBP). N-terminal MBP fusions to the ZFPs were constructed by PCR amplification of the pET15b clones and insertion into the vector pMal-c2 under the control of the Tac promoter (New England Biolabs). The fusion allows simple purification and detection of the recombinant protein. It had been reported previously that zinc finger DNA-binding proteins can be expressed from this vector in soluble form to high levels in *E. coli* and can bind efficiently to the appropriate DNA target without refolding (Liu et al. *PNAS* 94:5525–5530 (1997)). Production of MBP-fused proteins

```
VEGF1:                GGTACCCATACCTGGCAAGAAGAAGCAGCACATCTGCCACATCCAGGGCTGT    (SEQ ID NO:2)

GGTAAAGTTTACGGCACAACCTCAAATCTGCGTCGTCACCTGCGCTGGCACA

CCGGCGAGAGGCCTTTCATGTGTACCTGGTCCTACTGTGGTAAACGCTTCACC

CGTTCGTCAAACCTGCAGCGTCACAAGCGTACCCACACCGGTGAGAAGAAAT

TTGCTTGCCCGGAGTGTCCGAAGCGCTTCATGCGTAGTGACCACCTGTCCCGT

CACATCAAGACCCACCAGAATAAGAAGGGTGGATCC

VEGF 1 translation:   VPIPGKKKQHICHIQGCGKVYGTTSNLRRHLRWHTGERPMCTWSYCGKRFTRS   (SEQ ID NO:3)

SNLQRHKRTHTGEKKFACPECPKRFMRSDHLSRHIKTHQNKKGGS

VEGF3a:               GGTACCCATACCTGGCAAGAAGAAGCAGCACATCTGCCACATCCAGGGCTGT    (SEQ ID NO:4)

GGTAAAGTTTACGGCCAGTCCTCCGACCTGCAGCGTCACCTGCGCTGGCACA

CCGGCGAGAGGCCTTTCATGTGTACCTGGTCCTACTGTGGTAAACGCTTCACC

CGTTCGTCAAACCTACAGAGGCACAAGCGTACACACACCGGTGAGAAGAAA

TTTGCTTGCCCGGAGTGTCCGAAGCGCTTCATGCGAAGTGACGAGCTGTCAC

GACATATCAAGACCCACCAGAACAAGAAGGGTGGATCC

VEGF3a translation:   VPIPGKKKQHICHIQGCGKVYGQSSDLQRHLRWHTGERPFMCTWSYCGRFTRS   (SEQ ID NO:5)

SNLQRHKRTHTGEKKFACPECPKRFMRSDELSRHIKTHQNKKGGS
```

The ability of the designed ZFPs to bind their target sites was verified by expressing and purifying recombinant protein from *E. coli* and performing electrophoretic mobility shift assays (EMSAs). The expression of ZFPs was carried out in two different systems. In the first, the DNA-binding peptides were expressed in *E. coli* by inserting them into the commercially available pET15b vector (Novagen). This vector contains a T7 promoter sequence to drive expression of the recombinant protein. The constructs were introduced into *E. coli* BL21/DE3 ($lacI^q$) cells, which contain an IPTG-inducible T7 polymerase. Cultures were supplemented with 50 μM $ZnCl_2$, were grown at 37° C. to an OD at 600 nm of 0.5–0.6, and protein production was induced with IPTG for 2 hrs. ZFP expression was seen at very high levels, approximately 30% of total cellular protein. These proteins are referred to as "unfused" ZFPs.

Partially pure unfused ZFPs were produced as follows (adapted from Desjarlais & Berg, *Proteins: Structure, Function and Genetics* 12:101–104 (1992)). A frozen cell pellet was resuspended in 1/50th volume of 1 M NaCl, 25 mM Tris was as described by the manufacturer (New England Biolabs). Transformants were grown in LB medium supplemented with glucose and ampicillin, and were induced with IPTG for 3 hrs at 37° C. The cells were lysed by French press, then exposed to an agarose-based amylose resin, which specifically binds to the MBP moiety, thus acting as an affinity resin for this protein. The MBP fusion protein was eluted with 10 mM maltose to release ZFP of >50% purity. In some cases, the proteins were further concentrated using a Centricon 30 filter unit (Amicon).

Partially purified unfused and MBP fusion ZFPs were tested by EMSA to assess binding to their target DNA sequences. The protein concentrations in the preparations were measured by Bradford assay (BioRad). Since SDS polyacrylamide gels demonstrated >50% homogeneity by either purification method, no adjustment was made for ZFP purity in the calculations. In addition, there could be significant amounts of inactive protein in the preparations. Therefore, the data generated by EMSAs below represent an underestimate of the true affinity of the proteins for their targets (i.e., overestimate of $K_d$s). Two separate preparations were made for each protein to help control for differences in ZFP activity.

The VEGF DNA target sites for the EMSA experiments were generated by embedding the 9-bp binding sites in 29-bp duplex oligonucleotides. The sequences of the recognition ("top") strand and their complements ("bottom") used in the assays are as follows:

```
                                           (SEQ ID NO:6)
VEGF site 1, top:
5'-CATGCATAGCGGGGAGGATCGCCATCGAT
                                           (SEQ ID NO:7)
VEGF site 1, bottom:
5'-ATCGATGGCGATCCTCCCCGCTATGCATG
                                           (SEQ ID NO:8)
VEGF site 3, top:
5'-CATGCATATCGCGGAGGCTTGGCATCGAT VEGF site 3, bottom:
5'-ATCGATGCCAAGCCTCCGCGATATGCATG
```

(SEQ ID NO:9)

The VEGF DNA target sites are underlined. The 3 bp on either side of the 9 bp binding site was also derived from the actual VEGF DNA sequence. The top strand of each target site was labeled with polynucleotide kinase and γ-$^{32}$P ATP. Top and bottom strands were annealed in a reaction containing each oligonucleotide at 0.5 μM, 10 mM Tris-HCl (pH 8.0), 1 mM EDTA, and 50 mM NaCl. The mix was heated to 95° C. for 5 min. and slow cooled to 30° C. over 60 min. Duplex formation was confirmed by polyacrylamide gel electrophoresis. Free label and ssDNA remaining in the target preparations did not appear to interfere with the binding reactions.

Binding of the ZFPs to target oligonucleotides was performed by titrating protein against a fixed amount of duplex substrate. Twenty microliter binding reactions contained 10 fmole (0.5 nM) 5' $^{32}$P-labeled double-stranded target DNA, 35 mM Tris HCl (pH 7.8), 100 mM KCl, 1 mM MgCl$_2$, 1 mM dithiothreitol, 10% glycerol, 20 μg/ml poly dI-dC (optionally), 200 μg/ml bovine serum albumin, and 25 μM ZnCl$_2$. Protein was added as one fifth volume from a dilution series made in 200 mM NaCl, 20 mM Tris (pH 7.5), 1 mM DTT. Binding was allowed to proceed for 30 min. at room temperature. Polyacrylamide gel electrophoresis was carried out at 4° C. using precast 10% or 10–20% Tris-HCl gels (BioRad) and standard Tris-Glycine running buffer containing 0.1 mM ZnCl$_2$.

A typical EMSA using an MBP fused ZFP was performed. In this case, a 3-fold dilution series of the MBP-VEGF1 protein was used. The shifted product was quantitated on a phosphorimager (Molecular Dynamics) and the relative signal (percent of plateau value) vs. the log$_{10}$ of nM protein concentration was plotted. An apparent $K_d$ was found by determining the protein concentration that gave half maximal binding of MBP-VEGF1 to its target site, which in this experiment was approximately 2 nM.

The binding affinities determined for the VEGF proteins can be summarized as follows. VEGF1 showed the stronger DNA-binding affinity; in multiple EMSA analyses, the average apparent $K_d$ was determined to be approximately 10 nM when bound to VEGF site 1. VEGF3a bound well to its target site but with a higher apparent $K_d$ than VEGF1; the average $K_d$ for VEGF3a was about 200 nM. In both cases the MBP-fused and unfused versions of the proteins bound with similar affinities. $K_d$s were also determined under these conditions for MBP fusions of the wild-type Zif268 and SP-1 ZFPs, which yielded $K_d$s of 60 and 65 nM, respectively. These results are similar to binding constants reported in the literature for Zif268 of approximately 2–30 nM (see, e.g., Jamieson et al., *Biochemistry* 33:5689–5695 (1994)). The $K_d$s for the synthetic VEGF ZFPs therefore compare very favorably with those determined for these naturally-occurring DNA-binding proteins.

In summary, this Example demonstrates the generation of two novel DNA-binding proteins directed to specific targets near the transcriptional start of the VEGF gene. These proteins bind with affinities similar to those of naturally-occurring transcription factors binding to their targets.

Example 2

If a zinc finger domain that recognizes a 9-bp target site lacks the necessary affinity or specificity when expressed inside cells, a larger domain can be constructed to recognize an 18 base-pair target site, by joining separate three-finger domains with a linker sequence to form a six-finger protein. This should ensure that a functional domain (e.g., activator or repressor) fused to the ZFP is specifically targeted to the appropriate sequence, particularly under conditions in which only small amounts of the ZFP fusion protein are being produced. The 9-bp target sites in VEGF were chosen to be adjacent to one another so that the zinc fingers could be linked to recognize an 18-bp sequence. The linker DGGGS was chosen because it permits binding of ZFPs to two 9-bp sites that are separated by a one nucleotide gap, as is the case for the VEGF1 and VEGF3a sites (see also Liu et al., *PNAS* 5525–5530 (1997)).

The 6-finger VEGF3a/1 protein encoding sequence was generated as follows. VEGF3a was PCR amplified using the primers SPE7 (5'-GAGCA GAATTCGGCAAGAAGAAGCAGCAC, SEQ ID NO:10) and SPEamp12 (5'-GTGG TCTAGACAGCTCGTCACTTCGC, SEQ ID NO:11) to generate EcoRI and XbaI restriction sites at the ends (restriction sites underlined). VEGF1 was PCR amplified using the primers SPEamp13 (5'- GGAG CCAAGGCTGTGGTAAAGTTTACGG. SEQ ID NO:12) and SPEamp11 (5'- GGAG AAGCTTGGATCCTCATTATCCC. SEQ ID NO:13) to generate StyI and HindIII restriction sites at the ends (restriction sites underlined). Using synthetic oligonucleotides, the following sequence was ligated between the XbaI and StyI sites, where XbaI and StyI are underlined: TCT AGA CAC ATC AAA ACC CAC CAG AAC AAG AAA GAC GGC GGT GGC AGC GGC AAA AAG AAA CAG CAC ATA TGT CAC ATC CAA GG (SEQ ID NO:14). This introduced the linker sequence DGGGS between the two SP-1 domains. The ligation product was reamplified with primers SPE7 and SPEamp11 and cloned into pUC19 using the EcoRI and HindIII sites. The linked ZFP sequences were then amplified with primers

```
                                          (SEQ ID NO:15)
(1) GB19
GCCATGCCGGTACCCATACCTGGCAAGAAGAAGCAGCAC
                                          (SEQ ID NO:16)
(2) GB10
CAGATCGGATCCACCCTTCTTATTCTGGTGGGT
``` to introduce KpnI and BamHI sites for cloning into the modified pMAL-c2 expression vector as described above.

The nucleotide sequence of the designed, 6-finger ZFP VEGF3a/1 from KpnI to BamHI is:

```
                                                  (SEQ ID NO:17)
GGTACCCATACCTGGCAAGAAGAAGCAGCACATCTGCCACATCCAGGGCT

GTGGTAAAGTTTACGGCCAGTCCTCCGACCTGCAGCGTCACCTGCGCTGG

CACACCGGCGAGAGGCCTTTCATGTGTACCTGGTCCTACTGTGGTAAACG

CTTCACACGTTCGTCAAACCTACAGAGGCACAAGCGTACACACAGGTG

AGAAGAAATTTGCTTGCCCGGAGTGTCCGAAGCGCTTCATGCGAAGTGAC

GAGCTGTCTAGACACATCAAAACCCACCAGAACAAGAAAGACGGCGGTGG

CAGCGGCAAAAAGAAACAGCACATATGTCACATCCAAGGCTGTGGTAAAG

TTTACGGCACAACCTCAAATCTGCGTCGTCACCTGCGCTGGCACACCGGC

GAGAGGCCTTTCATGTGTACCTGGTCCTACTGTGGTAAACGCTTCACCCG

TTCGTCAAACCTGCAGCGTCACAAGCGTACCCACACCGGTGAGAAGAAAT

TTGCTTGCCCGGAGTGTCCGAAGCGCTTCATGCGTAGTGACCACCTGTCC

CGTCACATCAAGACCCACCAGAATAAGAAGGGTGGATCC
```

The VEGF3a/1 amino acid translation (using single letter code) is:

```
                                                  (SEQ ID NO: 18)
VPIPGKKKQHICHIQGCGKVYGQSSDLQRHLRWHTGERPFMCTWSYCGKR

FTRSSNLQRHKRTHTGEKKFACPECPKRFMRSDELSRHIKTHQNKKDGGG

SGKKKQHICHIQGCGKVYGTTSNLRRHLRWHTGERPFMCTWSYCGKRFTR

SSNLQRHKRTHTGEKKFACPECPKRFMRSDHLSRHIKTHQNKKGGS
```

The 18-bp binding protein VEGF3a/1 was expressed in *E. coli* as an MBP fusion, purified by affinity chromatography, and tested in EMSA experiments as described in Example 1. The target oligonucleotides were prepared as described and comprised the following complementary sequences:

```
                                                  (SEQ ID NO:19)
(1) JVF9
AGCGAGCGGGGAGGATCGCGGAGGCTTGGGGCAGCCGGGTAG, and
                                                  (SEQ ID NO:20)
(2) JVF10
CGCTCTACCCGGCTGCCCCAAGCCTCCGCGATCCTCCCCGCT
```

For the EMSA studies, 20 µl binding reactions contained 10 fmole (0.5 nM) 5' $^{32}$P-labeled double-stranded target DNA, 35 mM Tris HCl (pH 7.8), 100 mM KCl, 1 mM MgCl$_2$, 5 mM dithiothreitol, 10% glycerol, 20 µg/ml poly dI-dC, 200 µg/ml bovine serum albumin, and 25 µM ZnCl$_2$. Protein was added as one fifth volume from a 3-fold dilution series. Binding was allowed to proceed for 60 min at either room temperature or 37° C. Polyacrylamide gel electrophoresis was carried out at room temperature or 37° C. using precast 10% or 10–20% Tris-HCl gels (BioRad) and standard Tris-Glycine running buffer. The room temperature assays yielded an apparent $K_d$ for this VEGF3a/1 protein of approximately 1.5 nM. Thus, the 18-bp binding ZFP bound with high affinity to its target site. In a parallel experiment, VEGF1 protein was tested against its target using the oligonucleotides described in Example 1, yielding an apparent $K_d$ of approximately 2.5 nM. When binding and electrophoresis were performed at 37° C., the apparent $K_d$ of VEGF3a/1 was approximately 9 nM when tested against the 18-bp target, compared to a $K_d$ of 40 nM for VEGF1 tested against its target. This indicates that the difference in binding affinities is accentuated at the higher temperature.

The apparent $K_d$ is a useful measure of the affinity of a protein for its DNA target. However, for a DNA binding site either in vitro or in vivo, its occupancy is determined to a large extent by the off-rate of the DNA-binding protein. This parameter can be measured by competition experiments. The conditions for EMSA were as described above; binding and electrophoresis were performed at 37° C. These data indicate that the half-life of the protein-DNA complex is more than ten times longer for VEGF3a/1 than for VEGF1. Thus, under these in vitro conditions, the occupancy of the target site is much higher for the 18-bp binding protein than for the 9-bp binding protein.

Example 3

This Example describes the construction of expression vectors for producing ZFPs within mammalian cells, translocating them to the nucleus, and providing functional domains that are localized to the target DNA sequence by the ZFP. The functional domains employed are the Kruppel-Associated Box (KRAB) repression domain and the Herpes Simplex Virus (HSV-1) VP16 activation domain.

Certain DNA-binding proteins contain separable domains that function as transcriptional repressors. Approximately 20% of ZFPs contain a non-DNA-binding domain of about 90 amino acids that functions as a transcriptional repressor (Thiesen, *The New Biologist* 2:363–374 (1990); Margolin et al., *PNAS* 91:4509–4513 (1994); Pengue et al., (1994), supra; Witzgall et al., (1994), supra). This domain, termed the KRAB domain, is modular and can be joined to other DNA-binding proteins to block expression of genes containing the target DNA sequence (Margolin et al., (1994); Pengue et al., (1994); Witzgall et al., (1994), supra). The KRAB domain has no effect by itself; it needs to be tethered to a DNA sequence via a DNA-binding domain to function as a repressor. The KRAB domain has been shown to block transcription initiation and can function at a distance of up to at least 3 kb from the transcription start site. The KRAB domain from the human KOX-1 protein (Thiesen, *The New Biologist* 2:363–37 (1990)) was used for the studies described here. This 64 amino acid domain can be fused to ZFPs and has been shown to confer repression in cell culture (Liu et al., supra).

The VP16 protein of HSV-1 has been studied extensively, and it has been shown that the C-terminal 78 amino acids can act as a trans-activation domain when fused to a DNA-binding domain (Hagmann et al., *J. Virology* 71:5952–5962 (1997)). VP16 has also been shown to function at a distance and in an orientation-independent manner. For these studies, amino acids 413 to 490 in the VP16 protein sequence were used. DNA encoding this domain was PCR amplified from plasmid pMSVP16 C+119 using primers with the following sequences:

```
                                                  (SEQ ID NO:21)
(1) JVF24
CGCGGATCCGCCCCCCCGACCGATG, and
                                                  (SEQ ID NO:22)
(2) JVF25
CCGCAAGCTTACTTGTCATCGTCGTCCTTGTAGTCGCTGCCCCCACCG

TACTCGTCAATTCC
```

The downstream primer, JVF25, was designed to include a downstream FLAG epitope-encoding sequence.

Three expression vectors were constructed for these studies. The vectors are derived from pcDNA3.1(+) (Invitrogen), and place the ZFP constructs under the control of the cytomegalovirus (CMV) promoter. The vector carries ampicillin and neomycin markers for selection in bacteria and mammalian cell culture, respectively. A Kozak sequence for proper translation initiation (Kozak, *J. Biol. Chem.* 266:19867–19870 (1991)) was incorporated. To achieve nuclear localization of the products, the nuclear localization sequence (NLS) from the SV40 large T antigen (Pro-Lys-Lys-Lys-Arg-Lys-Val, SEQ ID NO:40) (Kalderon et al., *Cell* 39:499–509 (1984)) was added. The insertion site for the ZFP-encoding sequence is followed by the functional domain sequence. The three versions of this vector differ in the functional domain; "pcDNA-NKF" carries the KRAB repression domain sequence, "pcDNA-NVF" carries the VP16 activation domain, and "NF-control" carries no functional domain. Following the functional domain is the FLAG epitope sequence (Kodak) to allow specific detection of the ZFPs.

The vectors were constructed as follows. Plasmid pcDNA-HB was constructed by digesting plasmid pcDNA3.1(+) (Invitrogen, Carlsbad, Calif.) with HindIII and BamHI, filling in the sticky ends with Klenow, and religating. This eliminated the HindIII, KpnI, and BamHI sites in the polylinker. The vector pcDNA3.1(+) is described in the Invitrogen catalog. Plasmid pcDNA-NKF was generated by inserting a fragment into the EcoRI/XhoI sites of pcDNA-HB that contained the following: 1) a segment from EcoRI to KpnI containing the Kozak sequence including the initiation codon and the SV40 NLS sequence, altogether comprising the DNA sequence (SEQ ID NO:23)
GAATTCGCTAGCGCCACCATGGCCCCCAAGAAGAAGAGGAAGGTGGGAATCCATGGGGTAC, where the EcoRI and KpnI sites are underlined; and 2) a segment from KpnI to XhoI containing a BamHI site, the KRAB-A box from KOX1 (amino acid coordinates 11–53 in Thiesen, 1990, supra), the FLAG epitope (from Kodak/IBI catalog), and a HindIII site, altogether comprising the sequence (SEQ ID NO:24)
GGTACCCGGGGATCCCGGACACTGGTGACCTTCAAGGATGTATTTGTGGA

CTTCACCAGGGAGGAGTGGAAGCTGCTGGACACTGCTCAGCAGATCGTGT

ACAGAAATGTGATGCTGGAGAACTATAAGAACCTGGTTTCCTTGGGCAGC

GACTACAAGGACGACGATGACAAGTAAGCTTCTCGAG where the KpnI, BamHI and XhoI sites are underlined.

The VEGF3a/1-KRAB effector plasmid was generated by inserting a KpnI-BamHI cassette containing the ZFP sequences into pcDNA-NKF digested with KpnI and BamHI. The VEGF1-KRAB and VEGF3a-KRAB effector plasmids were constructed in a similar way except that the ZFP sequences were first cloned into the NLS-KRAB-FLAG sequences in the context of plasmid pLitmus 28 (New England Biolabs) and subsequently moved to the BamHI-XhoI sites of pcDNA3.1(+) as a BglII-XhoI cassette, where the BglII site was placed immediately upstream of the EcoRI site (see Example 4 for expression of these vectors).

The effector plasmids used in Example 5 were constructed as follows. Plasmid pcDNA-NVF was constructed by PCR amplifying the VP16 transactivation domain, as described above, and inserting the product into the BamHI/HindIII sites of pcDNA-NKF, replacing the KRAB sequence. The sequence of the inserted fragment, from BamHI to HindIII, was:

(SEQ 1ID NO:25)
GGATCCGCCCCCCCGACCGATGTCAGCCTGGGGGACGAGCTCCACTTAGA

CGGCGAGGACGTGGCGATGGCGCATGCCGACGCGCTAGACGATTTCGATC

TGGACATGTTGGGGGACGGGGATTCCCCGGGGCCGGGATTTACCCCCCAC

GACTCCGCCCCCTACGGCGCTCTGGATATGGCCGACTTCGAGTTTGAGCA

GATGTTTACCGATGCCCTTGGAATTGACGAGTACGGTGGGGGCAGCGACT

ACAAGGACGACGATGACAAGTAAGCTT

VEGF1-VP16 and VEGF3a/1-VP16 vectors-were constructed by inserting a KpnI-BamHI cassette containing the ZFP sequences into pcDNA-NVF digested with KpnI and BamHI.

The effector plasmids used in Example 6 were constructed as follows. Plasmid NF-control was generated by inserting the sequence (SEQ ID NO:26)
GAATTCGCTAGCGCCACCATGGCCCCCAAGAAGAAGAGGAAGGTGGGAA

TCCATGGGGTACCCGGGGATGGATCCGGCAGCGACTACAAGGACGACGAT

GACAAGTAAGCTTCTCGAG into the EcoRI-XhoI sites of pcDNA-NKF, thereby replacing the NLS-KRAB-FLAG sequences with NLS-FLAG only.

VEGF1-NF and VEGF3a/1-NF were constructed by inserting a KpnI-BamHI cassette containing the ZFP sequences into NF-control digested with KpnI and BamHI. CCR5-KRAB was constructed in the same way as the VEGF KRAB vectors, except that the ZFP sequences were designed to be specific for a DNA target site that is unrelated to the VEGF targets.

Finally, control versions of both the KRAB and VP16 expression plasmids were constructed. Plasmid NKF-control was designed to express NLS-KRAB-FLAG without zinc finger protein sequences; plasmid NVF-control was designed to express NLS-VP16-FLAG without ZFP sequences. These plasmids were made by digesting pcDNA-NKF and -NVF, respectively, with BamHI, filling in the ends with Klenow, and religating in order to place the downstream domains into the proper reading frame. These plasmids serve as rigorous controls for cell culture studies.

Mammalian cell expression and nuclear localization of the VEGF engineered ZFPs was demonstrated through immunofluorescence studies. 293 (human embryonic kidney) cells were transfected with the expression plasmid encoding the NLS-VEGF1-KRAB-FLAG chimera. Lipofectamine was used as described below. After 24-48 hours, cells were fixed and exposed to a primary antibody against the FLAG epitope. A secondary antibody labeled with Texas Red was applied, and the cells were counter stained with DAPI. Texas Red staining was observed to consistently co-localize with the DAPI staining, indicating that the ZFP being expressed from this plasmid was nuclear localized.

Example 4

This Example demonstrates the use of transient co-transfection studies to measure the activity of the ZFP repressor proteins in cells. Such experiments involve co-transfection of ZFP-KRAB expression ("effector") plasmids with reporter plasmids carrying the VEGF target sites. Efficacy is assessed by the repression of reporter gene expression in the presence of the effector plasmid relative to empty vector controls.

The reporter plasmid system was based on the pGL3 firefly luciferase vectors (Promega). Four copies of the VEGF target sites were inserted upstream of the SV40 promoter, which is driving the firefly luciferase gene, in the plasmid pGL3-Control to create pVFR1–4x. This plasmid contains the SV40 enhancer and expresses firefly luciferase to high levels in many cell types. Insertions were made by ligating together tandem copies of the two complementary 42-bp oligonucleotides, JVF9 and JVF10, described in Example 2. Adaptor sequences were ligated on, and the assembly was inserted into the MluI/BglII sites of pGL3-Control. This resulted in the insertion of the following sequence between those sites:

(SEQ ID NO:27)
ACGCGTaagcttGCTAGCGAGCGGGGAGGATCGCGGAGGCT

TGGGGCAGCCGGGTAGAGCGAGCGGGGAGGATCGCGGAGGCT

TGGGGCAGCCGGGTAGAGCGAGCGGGGAGGATCGCGGAGGCT

TGGGGCAGCCGGGTAGAGCGAGCGGGGAGGATCGCGGAGGCT

TGGGGCAGCCGGGTAGAGCGCTCAGaagcttAGATCT

The first six and last six nucleotides shown are the MluI and BglII sites; the lowercase letters indicate HindIII sites. The binding sites for VEGF1 and VEGF3a are underlined.

The effector plasmid construction is described above. The VEGF 1-KRAB, VEGF3a-KRAB, and VEGF3a/1-KRAB expression vectors were designed to produce a fusion of the SV40 nuclear localization sequence, the VEGF ZFP, the KRAB repression domain, and a FLAG epitope marker all under the control of the CMV promoter. The empty pcDNA3.1 expression vector was used as a control (pcDNA).

All vectors were prepared using Qiagen DNA purification kits. Approximately 40,000 cells were seeded into each well of a 24-well plate and allowed to grow overnight in Dulbecco's Modified Eagle Medium (D-MEM) medium containing 10% fetal bovine serum at 37° C. with 5% $CO_2$. Cells were washed with PBS and overlayed with 200 µl of serum-free D-MEM. Plasmids were introduced using lipofectamine (Gibco-BRL). Each well was transfected with about 0.3 µg of effector plasmid, 0.3 µg of reporter plasmid, and 0.01 µg of plasmid pRL-SV40 (Promega) that had been complexed with 6 µl of lipofectamine and 25 µl of D-MEM for 30 min at 37° C. Transfections were done in triplicate. After 3 hrs, 1 ml of medium containing 10% serum was added to each well. Cells were harvested 40–48 hours after transfection. Luciferase assays were done using the Dual Luciferase System (Promega). The third plasmid transfected, pRL-SV40, carries the *Renilla* luciferase gene and was co-transfected as a standard for transfection efficiency.

For the control reporter plasmid pGL3-Control (pGL3-C), the presence or absence of the ZFP-KRAB expression plasmid does not influence the luciferase expression level. However, for pVFR1-4x, the reporter containing four copies of the VEGF target site, presence of the VEGF1 (9-bp-binding ZFP) or VEGF3a/1 (18-bp-binding ZFP) expression plasmid reduces luciferase expression by a factor of 2–3 relative to the empty pcDNA vector control. The VEGF3a (9-bp-binding ZFP) expression plasmid appears to exhibit little or no effect. These experiments clearly demonstrate that a designed ZFP is capable of functioning in a cell to repress transcription of a gene when its target site is present. Furthermore, it appears that a certain level of affinity is required for function; i.e., VEGF1 and VEGF3a/1, with $K_d$s of 10 nM or less, are functional, whereas VEGF3a, with a $K_d$ of 200 nM, is not.

A second reporter plasmid, pVFR2-4x, was constructed by removing the four copies of the VEGF target sites using HindIII and inserting them into the HindIII site of pGL3-Control (in the forward orientation). This places the target sites between the start site of transcription for the SV40 promoter and the translational start codon of the luciferase gene. In co-transfection experiments similar to those described, approximately 3–4 fold repression of the luciferase signal was observed with the VEGF1-KRAB or VEGF3a/1-KRAB repressors relative to the pcDNA controls. This indicates that the repressors are active when bound either upstream or downstream of the start of transcription.

Example 5

This Example demonstrates the use of transient co-transfection studies to measure the activity of the ZFP transcriptional activators in cells. The experimental setup is similar to that of Example 4 except that a different transfection method, a different cell line, and a different set of reporter and effector plasmids were used.

For activation experiments, a reporter was constructed labeled pVFR3-4x. This reporter contains the four copies of the VEGF targets, with the sequence shown above, at the MluI/BglII sites of plasmid pGL3-Promoter (Promega). This vector has been deleted for the SV40 enhancer sequence and therefore has a lower basal level of firefly luciferase expression. pVFR3-4x was constructed by swapping the KpnI/NcoI fragment of pVFR1-4x into the KpnI/NcoI sites of pGL3-Promoter.

The effector plasmid construction is described above. The VEGF1-VP16, VEGF3a-VP16, and VEGF3a/1-VP16 expression vectors were designed to produce a fusion of the SV40 nuclear localization sequence, the VEGF ZFP, the VP16 trans-activation domain, and a FLAG epitope tag all under the control of the CMV promoter. The empty pcDNA3 expression vector was used as a control.

All vectors were prepared using Qiagen DNA purification kits. Approximately 40,000 cells were seeded into each well of a 24-well plate and allowed to grow overnight in D-MEM medium containing 10% fetal bovine serum at 37° C. with 5% $CO_2$. Cells were washed with serum-free D-MEM and overlayed with 200 µl of the same. Plasmids were introduced using a calcium phosphate transfection kit (Gibco-BRL) according to the manufacturer's instructions. Cells in each well were transfected with 1.5 µg of reporter plasmid, 1.5 µg of effector plasmid, and 0.5 µg of an actin/β-gal plasmid. Plasmids were combined with 15 µl of $CaCl_2$ and brought to 100 µl with $dH_2O$. 100 µl of HEPES solution was added dropwise while vortexing. The mix was incubated for 30 min at room temperature. The 200 µµl of calcium phosphate-treated DNA was then added to the medium in each well. Transfections were done in triplicate. After 5 hours, the medium was removed and 1 ml of medium containing 10% serum was added. Cells were harvested 40–48 hours after transfection. Luciferase assays were done using the Dual-Light system (Tropix). The third plasmid transfected, actinβ- gal, carries the β-galactosidase gene under the control of the actin promoter and was co-transfected as a standard for transfection efficiency. The β-galactosidase assays were also done according to the manufacturer's protocol (Tropix).

For the control reporter plasmid, pGL3-Promoter (pGL3-P), the presence or absence of the ZFP-VP16 expression plasmid does not significantly influence the luciferase expression level. For pVFR3-4x, the reporter containing four copies of the VEGF target site, presence of VEGF1 (the 9-bp-binding ZFP) shows a very slight activation relative to the empty pcDNA vector control. VEGF3a/1 (the 18-bp-binding ZFP) expression plasmid activates luciferase expression very substantially, showing about a 14-fold increase relative to pcDNA. These experiments clearly demonstrate that a designed ZFP, when fused to the VP16 activation domain, is capable of functioning in a cell to activate transcription of a gene when its target site is present. Furthermore, these results clearly demonstrate that an 18-bp binding protein, VEGF3a/1, is a much better activator in this assay than a 9-bp binding VEGF1 protein. This could be a result of the improved affinity or decreased off-rate of the VEGF3a/1 protein.

A fourth VEGF reporter plasmid was constructed by cloning the KpnI/NcoI fragment of pVFR2-4x into pGL3-Promoter to create plasmid pVFR4-4x. Activation was observed in co-transfections using this reporter in combination with effector plasmids expressing the VEGF1-VP16 and VEGF3a/1-VP16 fusions. This indicates that these artificial trans-activators are functional when bound either upstream or downstream of the start of transcription.

These co-transfection data demonstrate that ZFPs can be used to regulate expression of reporter genes. Such experiments can serve as a useful tool for identifying ZFPs for further use as modulators of expression of endogenous molecular targets.

Example 6

This example demonstrates that a designed ZFP can repress expression of an endogenous cellular gene that is in its normal genomic and chromatin context. Specifically, effector plasmids expressing VEGF ZFPs fused to the KRAB repression domain were introduced into cells and were shown to down-regulate the VEGF gene.

Eukaryotic expression vectors were constructed that fuse the VEGF3a/1 and the VEGF1 ZFPs to the SV40 NLS and KRAB, as described above in Example 3. Transfections were done using Lipofectamine, a commercially available liposome preparation from GIBCO-BRL. All plasmid DNAs were prepared using Qiagen Midi DNA purification system. 10 μg of the effector plasmid was mixed with 100 μg of Lipofectamine (50 μl) in a total volume of 1600 μl of Opti-MEM. A pCMVbeta-gal plasmid (Promega) was also included in the DNA mixture as an internal control for transfection efficiency. Following a 30 minute incubation, 6.4 ml of DMEM was added and the mixture was layered on $3 \times 10^6$ 293 cells. After five hours, the DNA-Lipofectamine mixture was removed, and fresh culture medium containing 10% fetal bovine serum was layered on the cells.

Eighteen hours post transfection, the 293 cells were induced by treatment with 100 μM DFX (desferrioxamine), resulting in a rapid and lasting transcriptional activation of the VEGF gene and also in a gradual increase in VEGF mRNA stability (Ikeda et al., *J. Biol. Chem.* 270:19761–19766 (1995)). Under routine culture conditions, 293 cells secrete a low level of VEGF in the culture media. The cells were allowed to incubate an additional 24 hours before the supernatants were collected for determination of VEGF levels by an ELISA assay.

In parallel experiments that demonstrated a similar level of repression, cell viability was monitored using the Promega Celltiter 96® Aqueous One Solution cell proliferation assay (Promega). After Dfx treatment for 18 hours, 500 μl of the original 2 ml of media was removed and analyzed for VEGF expression, as described above. To evaluate cell viability, 300 μl of Promega Celltiter 96® Aqueous One Solution Reagent was added to the remaining 1.5 ml. The cells were then incubated at 37° C. for approximately 2 hours. 100 μl from each well was transferred to a 96-well plate and read on an ELISA plate reader at OD 490 nm. There was no significant reduction in viability of cells expressing the VEGF3a/1-KRAB construct relative to those transfected with empty vector controls, indicating that the VEGF repression observed was not due to generalized cell death.

A 40–50-fold decrease in VEGF expression was noted in the DFX treated cells transfected with VEGF3a/1-KRAB, an expression vector encoding the 18 bp binding VEGF high affinity ZFP. A two-fold decrease in expression was observed when cells were transfected with VEGF 1-KRAB, an expression vector encoding the 9 bp binding VEGF high affinity ZFP. No significant decrease in VEGF expression was observed in cells that were transfected with a non-VEGF ZFP(CCR5-KRAB) or NKF-control. Similar results have been obtained in three independent transfection experiments.

In a separate experiment, the following results were obtained (data not shown). VEGF1-NF, which expresses the 9-bp-binding VEGF1 ZFP without a functional domain, showed no effect on VEGF gene expression. A significant reduction in VEGF expression was observed with VEGF3a/1-NF, which expresses the 18-bp binding protein without a functional domain. This result suggests that binding to the start site of transcription, even without a repression domain, interferes with transcription. Even when fused to the KRAB domain, the VEGF3a ZFP is unable to affect expression levels (plasmid VEGF3a-KRAB). However, VEGF1 fused to KRAB (VEGF1-KRAB) results in a dramatic decrease in expression. VEGF3a/1 fused to KRAB (VEGF3a/1-KRAB) prevents expression of VEGF altogether.

These data indicate that a designed ZFP is capable of locating and binding to its target site on the chromosome and preventing expression of an endogenous cellular target gene. In particular, the results indicate that ZFPs with a $K_d$ of less than about 25 nM (e.g., VEGF1 has an average apparent $K_d$ of about 10 nM) provide dramatic decreases in expression. In addition, the data demonstrate that the KRAB functional domain enhances gene silencing. Because in this experiment the introduction of the repressor occurs before the inducer of VEGF is added (DFX), the data demonstrate the ability of a designed repressor to prevent activation of an already quiescent gene. In addition, these results demonstrate that a six-finger engineered ZFP (VEGF3a/1) with nanomolar affinity for its target is able to inhibit the hypoxic response of the VEGF gene when it binds a target that overlaps the transcriptional start site.

Example 7

This Example demonstrates that a designed ZFP can activate the expression of an endogenous cellular gene that is in its normal genomic and chromatin context. Specifically, effector plasmids expressing VEGF ZFPs fused to the VP16 activation domain were introduced into cells and were shown to up-regulate the VEGF gene.

Eukaryotic expression vectors were constructed that fuse the VEGF3a/1 and the VEGF1 ZFPs to the SV40 NLS and VP16, as described in Example 3. Transfections were done using Lipofectamine, a commercially available liposome preparation from GIBCO-BRL. All plasmid DNAs were prepared using the Qiagen Midi DNA purification system. 10 μg of the effector plasmid (containing the engineered ZFP) was mixed with 100 μg of Lipofectamine (50 μl) in a total volume of 1600 μl of Opti-MEM. A pCMVbeta-gal plasmid (Promega) was also included in the DNA mixture as an internal control for transfection efficiency. Following a 30 minute incubation, 6.4 ml of DMEM was added and the mixture was layered on $3 \times 10^6$ 293 cells. After five hours, the DNA-Lipofectamine mixture was removed, and fresh culture medium containing 10% fetal bovine serum was layered on the cells. One day later, fresh media was added and the supernatant was collected 24 hours later for determination of VEGF levels using a commercially available ELISA kit (R and D Systems).

For the three-fingered VEGF 1-specific ZFP (VEGF 1-VP16), a 7–10 fold increase in VEGF expression was observed when compared to control plasmid (NVF-control) and mock transfected cells. Similar results have been obtained in 5 independent experiments. It is important to note that the level of VEGF secretion in VEGF1-VP16 transfected cells was equivalent or greater than the level in cells that have been treated with DFX. Introduction of VEGF3a/1-VP16 stimulated a more modest induction of VEGF. This result is consistent with the finding in Example 6, in which expression of the 18-bp binding protein without a functional domain prevented activation to a certain degree. This result suggested that the tight binding of this protein to the start site of transcription interferes with activation.

These data indicate that a designed ZFP is capable of locating and binding to its target site on the chromosome, presenting a transcriptional activation domain, and dramatically enhancing the expression level of an endogenous gene. In particular, the results indicate that ZFPs with a $K_d$ of less than about 25 nM (e.g., VEGF1 has an average apparent $K_d$ of about 10 nM) provide dramatic increases in expression.

Example 8

To further substantiate the results in Examples 6 and 7, a ribonuclease protection assay (RPA) was performed to correlate the increased level of VEGF protein with an increase in VEGF mRNA levels (Example 7), and to correlate the decreased level of VEGF protein with a decrease in VEGF mRNA levels (Example 6).

RNA was isolated from the transfected cells using an RNA isolation kit (Pharmingen). Radiolabeled multi template probes, which included a VEGF specific probe, were prepared by in vitro transcription and hybridized overnight at 56° C. to 5 μg of each of the RNAs from the experimental and control transfected cells. The hybridization mixture was treated with RNase and the protected probes were purified and subjected to 5% denaturing polyacrylamide gel electrophoresis and the radioactivity was evaluated by autoradiography. 293 cells transfected with the VEGF1-VP16 had a 2–4 fold increase in the level of VEGF mRNA when compared to cells transfected with NVF-control (see Example 7 for experimental details). The size of the protected probe was identical to the size of the probe generated from the control human RNA provided as a control for RNA integrity.

In a separate experiment, the level of VEGF specific mRNA was also quantitated in cells that had been transfected with a VEGF-KRAB effector plasmid (see Example 6 for experimental details). The details of the transfection are described in Example 6. A dramatic decrease in the level of VEGF mRNA was observed when cells were transfected with the VEGF3a/1-KRAB effector plasmid. No significant decrease in VEGF mRNA was observed when cells were transfected with NKF-control or a non-VEGF specific ZFP (CCR5-5-KRAB and CCR5-3-KRAB, which recognize different CCR5 target sites).

This experiment demonstrates that the increase in VEGF protein observed upon transfection with the VEGF 1-VP 16 chimeric transcription factor is mediated by an increase in the level of VEGF mRNA. Similarly, the decrease in VEGF protein observed upon transfection with the VEGF3a/1-KRAB chimeric transcription factor is mediated by a decrease in the level of VEGF mRNA.

Example 9

Identification of Inhibitors of the VEGFR2-mediated Mitogenic Signal

Step 1: Production of Cell Lines

An ECV304-derived cell line that over-expresses VEGF-R2 and does not express VEGF-R1 is produced as follows. ZFP-repressors designed against VEGF-R1 are produced as described above. ZFP-activators designed to enhance VEGF-R2 also are generated. ECV304 cells are co-transfected with the two ZFP constructs; clones are picked for FACS analysis (R&D Systems, NFVE0) following drug-selection. A clone exhibiting a lack of VEGF-R1 and an increase in VEGF-R2 on the membrane surface via FACS analysis is expanded and the cell line is carried on for high throughput (HTP) screenings. This cell line is renamed VEGF-R1-/R2++.

A control cell line that constitutively represses VEGF-R1 and conditionally produces VEGF-R2 is produced as follows. ZFP-repressors designed against VEGF-R2 are cloned into the T-Rex® (Invitrogen) plasmid. This and the VEGF-R1 ZFP-repressors are co-transfected into ECV304 cells. Once again, a stable clone is selected and analyzed for a lack of VEGF-R1 and presence of VEGF-R2 via FACS analysis. The cells are then treated with doxycycline and examined for a loss of VEGF-R2 via FACS analysis. The cell line that does not express VEGF-R1 and shows a loss of VEGF-R2 following doxycycline treatment is carried forward for HTP screenings. This cell line is renamed VEGF-R1-/R2ind.

2. Starting with VEGF-R1-/R2++, plate 10,000 cells/per well in a 96-well plate. Because the final volume of the assay will be 100 μl, cells are plated in 50 μl of media.

3. The test compound from the compound library is added (25 μl) to a final concentration of 30 nM and the plates are incubated for one hour. 25 μl of media is added without any compounds to one well to serve as the +VEGF control. To another well, add 0.075 ng in 25 μl of TGFβ (R&D Systems, 100-B-001) for a final concentration of 1 ng/ml, to serve as a VEGF-inhibitor control.

4. Add VEGF (R&D Systems, 298-vs-005), 3 ng in 25 μl for a final concentration of 30 ng/ml, to each well. Incubate for 30 minutes.

5. Assay for phosphorylated tyrosines within the cells by permeabilizing the membrane. An alternative assay that measures protein tyrosine kinase activity is also available, skip to step 17.

6. Aspirate off media. Fix cells with 1% formaldehyde for 30 minutes.

7. Wash cells with PBS.

8. Add anti-phosphotyrosine antibody (Pierce, #29926), for a final concentration of 5 µg/ml. Incubate for 1 hour.

9. Wash cells with PBS containing 1% BSA and 0.05% NP-40.

10. Add goat-anti-mouse-IgG-HRP conjugate (Pierce, #31430), 1:200 dilution. Incubate for 1 hour.

11. Wash cells as above.

12. Perform HRP ELISA assay as described (Pierce, #32052). Identify compounds that reduce VEGF-stimulated phosphotyrosine production.

13. Prepare for secondary screen by plating VEGF-R 1-/R2ind-cells as in step 2, this time preparing duplicate plates.

14. To one plate, add doxycycline to a final concentration of 1 µg/ml. Incubate overnight.

15. To both plates, repeat steps 3–11.

16. A positive hit shows reduced VEGF-stimulated phosphotyrosine production in the non-doxycycline treated cells. The ideal compound behaves the same in the doxycycline-treated cells, thus demonstrating that it is not working on any systems other than the VEGF-R2-induced pathway.

17. Resuming from step 5. Aspirate off media. Solubilize cells by adding 200 µl of PTK extraction buffer (Promega, V6480) containing 1% Triton X-100) and incubate on ice for 10 minutes.

18. Detach any residual cells and mix the cell suspension several times by pipetting up and down several times. Transfer suspension into a deep well block and rock for 15 minutes at 4° C.

19. Centrifuge the suspension at 100,000×g at 4° C. for 1 hour and save the supernatant.

20. Continue with Step III.A.1 of the PTK Assay Protocol as described by Promega (technical bulletin TB211).

Example 10

Identification of Stimulants of T Cell Proliferation that do not Cause Activation of the T Cells Potassium channels play a critical role in modulating calcium signaling of T lymphocytes. The two predominant potassium channels expressed in human T lymphocytes are Kv1.3, a channel that opens in response to changes in membrane potential, and KCa4, a channel activated by elevations in intracellular calcium levels. Kv1.3 has been shown to play a vital role in controlling T cell proliferation, whereas KCa4 functions in T cell activation. Activation of the T cell then leads to the release of IFN-γ and an immune response. The caveat to this pathway is that KCa4 is up-regulated in response to known mitogenic and antigenic stimuli, thus, it has been difficult to identify compounds that can selectively allow for the proliferation of T lymphocytes but do not cause activation of the T cells. Although some KCa4 inhibitors have been identified, these inhibitors are not completely selective; they can also inhibit other proteins such as the calcium-release-activated Ca2+ (CRAC) channels, which also reside in T cells.

A ZFP-based inhibitor of the human hKCa4 gene was created using the methods of ZFP design described above. Its target sequence is located at basepair 217 of the cDNA sequence (Genbank Accession #AE022797). The target sequence is 5'-GGGGAGGGC-3' (SEQ ID NO:41). The amino acid sequences (in single letter code) of the recognition helices (form −1 to +6) are as follows: F1=RSDHLAR (SEQ ID NO:42). F2=RSDNLAR (SEQ ID NO:43). F3=RSDHLSR (SEQ ID NO:44).

The resulting 3-finger ZFP, called ZFP3A, has a dissociation constant of 0.3 nM for its target as measured by gel mobility shift assay. A VP16 fusion to the ZFP3A DNA binding domain activates a cotransfected reporter gene by greater than 5-fold.

A KRAB-ZFP3A chimeric construct to effect the inhibition of hKCa4 gene expression was cotransfected into human erythroleukemic cells along with an expression vector encoding green fluorescent protein (GFP). Transfected cells were identified using a fluorescence microscope. Transfected cells were then examined for hKCa4 function by the patch clamp method. Ion channel function was determined by determining the slope conductance (nS). Untransfected controls had a value of 12.5 (n=1). Cells transfected with an empty vector had a value of 10.0±2.5 (n=4). Cells transfected with ZFP3A had a value of 1.0±0.1 indicating almost total loss of function.

The ZPF3A-transfected cells are further transfected with a second ZFP designed to activate Kv1.3 expression. The sequence encoding the activator is cloned in the T-Rex™ (Invitrogen) plasmid. Stable clones are selected using FACS analysis to identify those clones that have an increased expression of Kv1.3. The clones are examined for changes in intracellular calcium fluctuations when treated with or without doxycycline (1 µg/mL) using the FLIPR®I Flouro-metric Imaging Plate Reader Systems (Molecular Dynamics). In the presence of doxycycline, there are minimal changes in the intracellular calcium fluctuations, whereas the non-doxycycline treated cells exhibit fluctuations similar to wild-type Jurkats. The cell line that has an increased expression of Kv1.3 and shows a loss of KCa4 following doxycycline treatment is carried forward for HTP screenings. It is renamed Kv1.3$^+$/KCa4$^{+/-}$.

Kv1.3$^+$/KCa4$^{+/-}$ cells are plated, in duplicate, at 10,000 cells/well in 96-well dishes. Doxycycline is added to a final concentration of 1 µg/mL to one plate, and both plates are incubated overnight.

The test compounds from the compound library are added to a final concentration of 30 nM to both plates and incubated for 24 hours. For each plate, a control well has 10 µg/mL of Concanavalin A (Con A, Amersham Pharmacia) to serve as the positive control for mitogenic activity and T cell activation. A second control well has nothing added to serve as the background control.

Four hours prior to harvesting, [$^3$H]thymidine (1 µCi/well) is added to each well.

The plates are spun to pellet the cells. Supernatants are collected for use in IFN-γ ELISA (protocol and reagents from Amersham Pharmacia).

Cells are resuspended in PBS and harvested onto glass fiber filters. [$^3$H]thymidine incorporation is measured in a scintillation counter.

The cells not exposed to any mitogenic compound serve as the baseline for [$^3$H]thymidine uptake and IFN-γ secretion. The Con A control exhibits an increased [$^3$H]thymidine uptake in both doxycycline-treated and non-treated cells; additionally, there is an increase in secreted IFN-γ in the non-treated cells but not in the doxycycline-treated cells. A positive hit is a compound that stimulates an increase in [$^3$H]thymidine incorporation but not IFN-γ secretion in either doxycycline-treated or non-treated cells.

Example 11

ZFP-Modulation of the Human Erythropoietin (EPO) Gene

In this example, the human erythropoietin (EPO) gene was used as an example of a molecular target whose expression can be modulated by a ZFP. Accordingly, a stable cell line comprising an inducible ZFP was established as described in Zhang et al. (2000) *J. Biol Chem* 275:33850–33860. The cell line contained a stably-integrated fusion gene encoding a ZFP DNA binding domain designed to bind a target site 862 nucleotides upstream of the human EPO gene (EPOZFP-862) fused to a VP16 activation domain. Expression of this fusion gene was under the control of tet transcriptional control sequences; and thus was inducible by doxycycline.

The target site for the EPOZFP-862 protein was GCG-GTGGCTC (SEQ ID NO: 36). The amino acid sequences of its recognition helices (between positions −1 and +6 inclusive) were F1: QSSDLTR (SEQ ID NO: 37); F2: RSDALSR (SEQ ID NO: 38); and F3: RSDERKR (SEQ ID NO: 39). The EPOZFP-862 zinc finger protein was designed in an SP-1 backbone, its gene was assembled by PCR, purified as a fusion with the maltose-binding protein and tested for its affinity for its target site as described supra.

Transient and stably transfected human embryonic kidney (HEK293) cells were generated as described in Zhang et al. (2000), supra. Briefly, the cells were grown in Dulbecco's modified Eagle's medium supplemented with 10% fetal calf serum. To generate stable Tet-inducible EPOZFP cell lines, the coding region from the pEPOZFP862 DNA was subcloned into pcDNA4/TO (Invitrogen) using AflIII and HindIII restriction sites. The resulting pTO-EPOZFP862 construct was transfected into the T-Rex-293™ (Invitrogen) cell line using LipofectAMINE (Life Technologies, Inc.). After 2 weeks of selection in medium containing Zeocin™ (Invitrogen), stable clones were isolated and analyzed for doxycycline (Dox)-dependent activation of ZFP expression.

Transient transfection was carried out using LipofectAMINE. Cell lysates were harvested 40 h after transfection, and luciferase activities were measured by the Dual-Light luciferase and β-galactosidase reporter assay system (Tropix). To assay the activation of the endogenous chromosomal EPO gene, Northern analysis and Taqman analyses of EPO mRNA were carried out as described in detail in Zhang et al. supra.

Figure 2A:
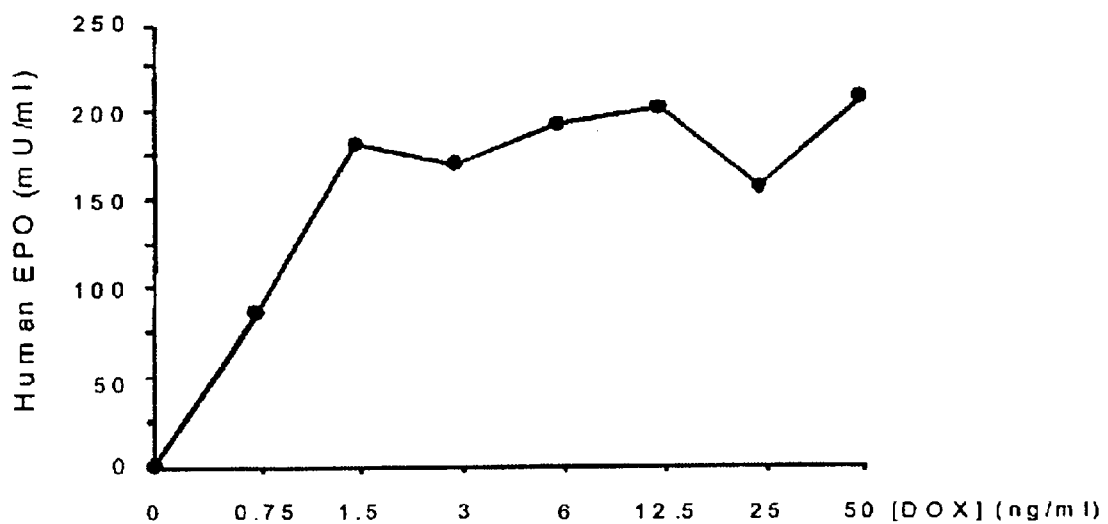
FIG. 2A shows the doxycycline (Dox) dose-response for EPO expression, as determined by ELISA.
Figure 2B:
FIG. 2B shows an immunoblot analysis of EPOZFP-862 expression in cells treated with the indicated concentration of doxycycline, using an anti-FLAG antibody.
Figure 2C:
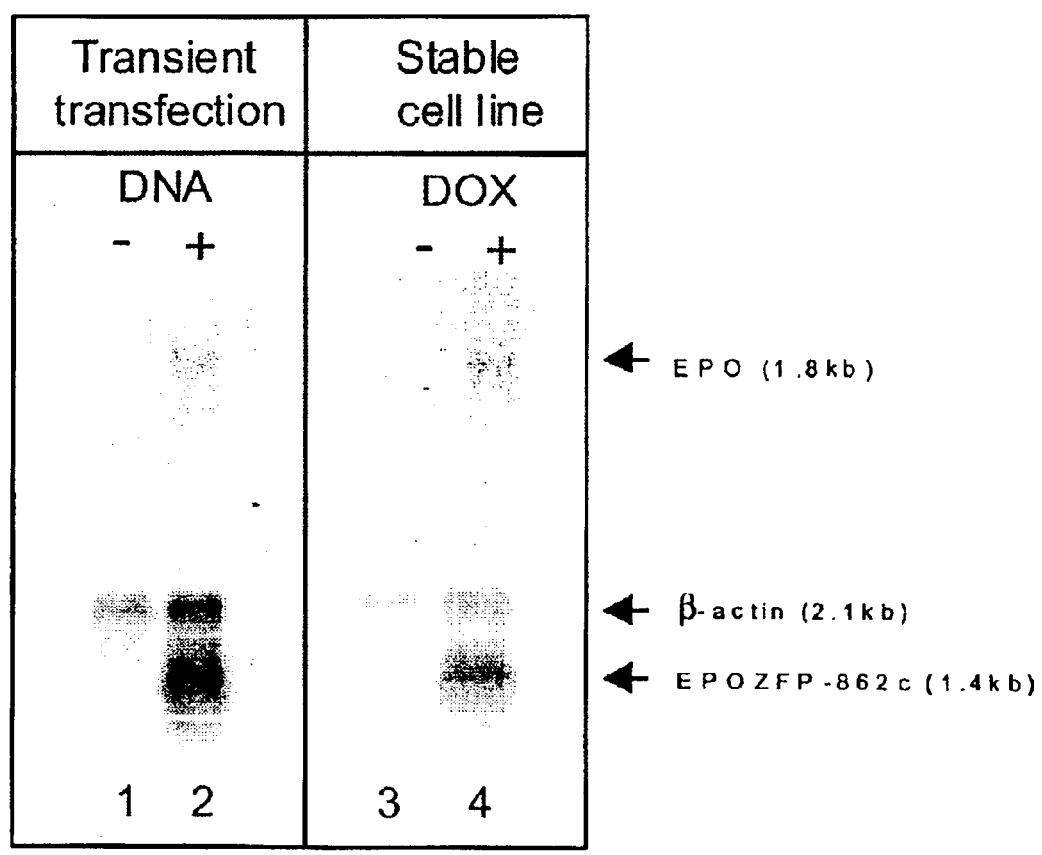
FIG. 2C shows Northern blot analysis of EPO mRNA induced by EPOZFP-862. Lane 1 is a control showing untransfected cells; lane 2 shows cells transiently transfected with EPOZFP-862; lanes 3 and 4 show cells stably transfected with EPOZFP-862, in the absence (lane 3) and presence (lane 4) of Dox.

As shown in FIG. 2, the endogenous EPO gene was inducibly expressed in response to synthesis of EPOZFP862. FIG. 2A shows EPO expression and the Dox dose-response curve for stably transformed 293 cells containing copies of the EPOZFP862 gene under control of a Tet-responsive full-length CMV promoter. For this experiment, conditioned medium was harvested 48 h after the addition of Dox (at the concentrations indicated in the figure) and analyzed by an EPO ELISA kit. FIG. 2B shows immunoblots of protein extracts from EPOZFP862 cells treated with the indicated Dox concentrations, using an anti-Flag antibody. Extracts were prepared from cells 48 h after induction. FIG. 2C shows RNA (Northern) blot analysis of EPO mRNA induced by EPOZFP862. EPO mRNA signals are shown for untransfected and EPOZFP862c-transfected 293 cells (lanes 1 and 2, respectively) and for uninduced and Dox-induced EPOZFP862 cells (lanes 3 and 4, respectively). The EPO probed membrane was stripped and rehybridized with a $^{32}$P-labeled riboprobe containing antisense fragments that hybridize to ZFP mRNA as well as to the human β-actin gene that served as a loading control.

Thus, endogenous human EPO can be activated in response to either transient or stable expression of a ZFP targeted to the EPO gene.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cell comprising a first polynucleotide encoding an exogenous zinc finger protein (ZFP) and further comprising a second polynucleotide encoding a reporter, wherein expression of the exogenous ZFP is regulated by a transcriptional control element that is responsive to a molecule involved in a cellular process; and wherein expression of the reporter is modulated by the ZFP.

2. The cell of claim 1, wherein the cellular process comprises a signal transduction pathway.

3. The cell of claim 1, wherein the first polynucleotide further comprises sequences encoding a functional domain operably linked to the zinc finger protein.

4. The cell of claim 3, wherein the functional domain is a repression domain.

5. The cell of claim 4, wherein the repression domain is selected from the group consisting of KRAB, MBD-2B, v-ErbA, MBD3, unliganded TR, and members of the DNMT family.

6. The cell of claim 1, wherein the reporter is selected from the group consisting of a direct reporter, an enzymatic reporter, a positive selection marker, a negative selection marker and combinations thereof.

7. The cell of claim 6, wherein the direct reporter is a fluorescent protein.

8. The cell of claim 7, wherein the direct reporter is green fluorescent protein.

9. The cell of claim 6, wherein the enzymatic reporter is selected from the group consisting of luciferase, beta-galactosidase, beta-glucuronidase, beta-lactamase, horseradish peroxidase, alkaline phosphatase and chloramphenicol acetyl transferase (CAT).

10. The cell of claim 6, wherein the positive selection marker is selected from the group consisting of neomycin resistance, G418 resistance, Zeocin® resistance and hygromycin resistance.

11. The cell of claim 6, wherein the negative selection marker is herpes simplex virus thymidine kinase (HSV-TK).

12. A kit for screening a compound for interaction with a molecular target, the kit comprising (a) a first cell according to claim 1; (b) a second cell substantially identical to the first cell but lacking the exogenous zinc finger protein; (c) ancillary reagants; (d) instructions and (e) suitable containers.

13. A kit for screening a compound for interaction with a molecular target, the kit comprising (a) a cell according to claim 1; (b) ancillary reagents; (c) instructions and (d) suitable containers.

14. The cell of claim 4, wherein the second polynucleotide comprises a constitutive promoter operably linked to the sequence encoding the reporter.

15. The cell of claim 14, wherein the repression domain is selected from the group consisting of KRAB, MBD-2B, v-ErbA, MBD3, unliganded TR, and members of the DNMT family.

16. The cell of claim 14, wherein the reporter or selectable marker is selected from the group consisting of a direct reporter, an enzymatic reporter, a positive selection marker, a negative selection marker and combinations thereof.

17. The cell of claim 16, wherein the direct reporter is a fluorescent protein.

18. The cell of claim 17, wherein the direct reporter is green fluorescent protein.

19. The cell of claim 16, wherein the enzymatic reporter is selected from the group consisting of luciferase, beta-galactosidase, beta-glucuronidase, beta-lactamase, horseradish peroxidase, alkaline phosphatase and chloramphenicol acetyl transferase (CAT).

20. The cell of claim 16, wherein the positive selection marker is selected from the group consisting of neomycin resistance, G418 resistance, Zeocin® resistance and hygromycin resistance.

21. The cell of claim 16, wherein the negative selection marker is herpes simplex virus thymidine kinase (HSV-TK).

22. A kit for screening a compound for interaction with a molecular target, the kit comprising (a) a cell according to claim 14; (b) ancillary reagents; (c) instructions and (d) suitable containers.

* * * * *

SEQUENCE LISTING

```
<160> NUMBER OF SEQ ID NOS: 45

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: human VEGF

<400> SEQUENCE: 1
agcggggagg atcgcggagg cttgg                                          25

<210> SEQ ID NO 2
<211> LENGTH: 298
<212> TYPE: DNA
<213> ORGANISM: Artificial Sequence
<220> FEATURE:
<223> OTHER INFORMATION: Description of Artificial Sequence: human SP-1

<400> SEQUENCE: 2
ggtacccata cctggcaaga agaagcagca catctgccac atccagggct gtggtaaagt    60
ttacggcaca acctcaaatc tgcgtcgtca cctgcgctgg cacaccggcg agaggccttt   120
catgtgtacc tggtcctact gtggtaaacg cttcacccgt tcgtcaaacc tgcagcgtca   180
```

```
caagcgtacc cacaccggtg agaagaaatt tgcttgcccg gagtgtccga agcgcttcat    240
gcgtagtgac cacctgtccc gtcacatcaa gacccaccag aataagaagg gtggatcc     298

<210> SEQ ID NO 3
<211> LENGTH: 99
<212> TYPE: PRT
<213> ORGANISM: Artificial Sequence
<220> FEATURE:
<223> OTHER INFORMATION: Description of Artificial Sequence: ZFP-VEGF1

<400> SEQUENCE: 3

Val Pro Ile Pro Gly Lys Lys Gln His Ile Cys His Ile Gln Gly
 1               5                  10                  15

Cys Gly Lys Val Tyr Gly Thr Thr Ser Asn Leu Arg Arg His Leu Arg
                20                  25                  30

Trp His Thr Gly Glu Arg Pro Phe Met Cys Thr Trp Ser Tyr Cys Gly
            35                  40                  45

Lys Arg Phe Thr Arg Ser Ser Asn Leu Gln Arg His Lys Arg Thr His
        50                  55                  60

Thr Gly Glu Lys Lys Phe Ala Cys Pro Glu Cys Pro Lys Arg Phe Met
    65                  70                  75                  80

Arg Ser Asp His Leu Ser Arg His Ile Lys Thr His Gln Asn Lys Lys
                85                  90                  95

Gly Gly Ser

<210> SEQ ID NO 4
<211> LENGTH: 298
<212> TYPE: DNA
<213> ORGANISM: Artificial Sequence
<220> FEATURE:
<223> OTHER INFORMATION: Description of Artificial Sequence: ZFP-VEGF3a

<400> SEQUENCE: 4
ggtacccata cctggcaaga agaagcagca catctgccac atccagggct gtggtaaagt    60
ttacggccag tcctccgacc tgcagcgtca cctgcgctgg cacaccggcg agaggccttt    120
catgtgtacc tggtcctact gtggtaaacg cttcacccgt cgtcaaaacc tacagaggca    180
caagcgtaca cacaccggtg agaagaaatt tgcttgcccg gagtgtccga agcgcttcat    240
gcgaagtgac gagctgtcac gacatatcaa gacccaccag aacaagaagg gtggatcc     298

<210> SEQ ID NO 5
<211> LENGTH: 99
<212> TYPE: PRT
<213> ORGANISM: Artificial Sequence
<220> FEATURE:
<223> OTHER INFORMATION: Description of Artificial Sequence: ZFP-VEGF3a

<400> SEQUENCE: 5

Val Pro Ile Pro Gly Lys Lys Gln His Ile Cys His Ile Gln Gly
 1               5                  10                  15

Cys Gly Lys Val Tyr Gly Gln Ser Ser Asp Leu Gln Arg His Leu Arg
                20                  25                  30

Trp His Thr Gly Glu Arg Pro Phe Met Cys Thr Trp Ser Tyr Cys Gly
            35                  40                  45

Lys Arg Phe Thr Arg Ser Ser Asn Leu Gln Arg His Lys Arg Thr His
        50                  55                  60

Thr Gly Glu Lys Lys Phe Ala Cys Pro Glu Cys Pro Lys Arg Phe Met
    65                  70                  75                  80
```

```
                        Arg Ser Asp Glu Leu Ser Arg His Ile Lys Thr His Gln Asn Lys Lys
                                     85                  90                  95

Gly Gly Ser

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: VEGF-1 top

<400> SEQUENCE: 6
catgcatagc ggggaggatc gccatcgat                                          29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: VEGF-1
      bottom

<400> SEQUENCE: 7
atcgatggcg atcctccccg ctatgcatg                                          29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: VEGF-3 top

<400> SEQUENCE: 8
catgcatatc gcggaggctt ggcatcgat                                          29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: VEGF-3
      bottom

<400> SEQUENCE: 9
atcgatgcca agcctccgcg atatgcatg                                          29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: primer SPE7

<400> SEQUENCE: 10
gagcagaatt cggcaagaag aagcagcac                                          29

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: primer
      SPEamp12

<400> SEQUENCE: 11
gtggtctaga cagctcgtca cttcgc                                             26
```

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: primer
      SPEamp13

<400> SEQUENCE: 12
ggagccaagg ctgtggtaaa gtttacgg                                          28

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: primer
      SPEamp11

<400> SEQUENCE: 13
ggagaagctt ggatcctcat tatccc                                            26

<210> SEQ ID NO 14
<211> LENGTH: 83
<212> TYPE: DNA
<213> ORGANISM: Artificial Sequence
<220> FEATURE:
<223> OTHER INFORMATION: Description of Artificial Sequence: linker Xba
      -Sty

<400> SEQUENCE: 14
tctagacaca tcaaaaccca ccagaacaag aaagacggcg gtggcagcgg caaaaagaaa       60
cagcacatat gtcacatcca agg                                               83

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: primer GB19

<400> SEQUENCE: 15
gccatgccgg tacccatacc tggcaagaag aagcagcac                              39

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: primer GB10

<400> SEQUENCE: 16
cagatcggat ccaccttct tattctggtg ggt                                     33

<210> SEQ ID NO 17
<211> LENGTH: 589
<212> TYPE: DNA
<213> ORGANISM: Artificial Sequence
<220> FEATURE:
<223> OTHER INFORMATION: Description of Artificial Sequence: ZFP-VEGF
      3a/1

<400> SEQUENCE: 17
ggtacccata cctggcaaga agaagcagca catctgccac atccagggct gtggtaaagt       60

```
ttacggccag tcctccgacc tgcagcgtca cctgcgctgg cacaccggcg agaggccttt      120
catgtgtacc tggtcctact gtggtaaacg cttcacacgt tcgtcaaacc tacagaggca      180
caagcgtaca cacacaggtg agaagaaatt tgcttgcccg gagtgtccga agcgcttcat      240
gcgaagtgac gagctgtcta gacacatcaa aacccaccag aacaagaaag acggcggtgg      300
cagcggcaaa aagaaacagc acatatgtca catccaaggc tgtggtaaag tttacggcac      360
aacctcaaat ctgcgtcgtc acctgcgctg gcacaccggc gagaggcctt tcatgtgtac      420
ctggtcctac tgtggtaaac gcttcacccg ttcgtcaaac ctgcagcgtc acaagcgtac      480
ccacaccggt gagaagaaat ttgcttgccc ggagtgtccg aagcgcttca tgcgtagtga      540
ccacctgtcc cgtcacatca agacccacca gaataagaag ggtggatcc                 589
```

```
<210> SEQ ID NO 18
<211> LENGTH: 196
<212> TYPE: PRT
<213> ORGANISM: Artificial Sequence
<220> FEATURE:
<223> OTHER INFORMATION: Description of Artificial Sequence: ZFP-VEGF
      3a/1

<400> SEQUENCE: 18
```

```
Val Pro Ile Pro Gly Lys Lys Gln His Ile Cys His Ile Gln Gly
 1               5                  10                  15

Cys Gly Lys Val Tyr Gly Gln Ser Ser Asp Leu Gln Arg His Leu Arg
                 20                  25                  30

Trp His Thr Gly Glu Arg Pro Phe Met Cys Thr Trp Ser Tyr Cys Gly
         35                  40                  45

Lys Arg Phe Thr Arg Ser Ser Asn Leu Gln Arg His Lys Arg Thr His
 50                  55                  60

Thr Gly Glu Lys Lys Phe Ala Cys Pro Glu Cys Pro Lys Arg Phe Met
 65                  70                  75                  80

Arg Ser Asp Glu Leu Ser Arg His Ile Lys Thr His Gln Asn Lys Lys
                 85                  90                  95

Asp Gly Gly Gly Ser Gly Lys Lys Lys Gln His Ile Cys His Ile Gln
            100                 105                 110

Gly Cys Gly Lys Val Tyr Gly Thr Thr Ser Asn Leu Arg Arg His Leu
        115                 120                 125

Arg Trp His Thr Gly Glu Arg Pro Phe Met Cys Thr Trp Ser Tyr Cys
130                 135                 140

Gly Lys Arg Phe Thr Arg Ser Ser Asn Leu Gln Arg His Lys Arg Thr
145                 150                 155                 160

His Thr Gly Glu Lys Lys Phe Ala Cys Pro Glu Cys Pro Lys Arg Phe
                165                 170                 175

Met Arg Ser Asp His Leu Ser Arg His Ile Lys Thr His Gln Asn Lys
            180                 185                 190

Lys Gly Gly Ser
        195
```

```
<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: primer JVF9

<400> SEQUENCE: 19
agcgagcggg gaggatcgcg gaggcttggg gcagccgggt ag                         42
```

```
<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: primer
      JVF10

<400> SEQUENCE: 20
cgctctaccc ggctgcccca agcctccgcg atcctccccg ct                    42

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: primer
      JVF24

<400> SEQUENCE: 21
cgcggatccg ccccccgac cgatg                                        25

<210> SEQ ID NO 22
<211> LENGTH: 62
<212> TYPE: DNA
<213> ORGANISM: Artificial Sequence
<220> FEATURE:
<223> OTHER INFORMATION: Description of Artificial Sequence: primer
      JVF25

<400> SEQUENCE: 22
ccgcaagctt acttgtcatc gtcgtccttg tagtcgctgc ccccaccgta ctcgtcaatt    60
cc                                                                  62

<210> SEQ ID NO 23
<211> LENGTH: 61
<212> TYPE: DNA
<213> ORGANISM: Artificial Sequence
<220> FEATURE:
<223> OTHER INFORMATION: Description of Artificial Sequence: SV40 NLS

<400> SEQUENCE: 23
gaattcgcta gcgccaccat ggccccccaag aagaagagga aggtgggaat ccatggggta   60
c                                                                   61

<210> SEQ ID NO 24
<211> LENGTH: 187
<212> TYPE: DNA
<213> ORGANISM: Artificial Sequence
<220> FEATURE:
<223> OTHER INFORMATION: Description of Artificial Sequence: KRAB-FLAG

<400> SEQUENCE: 24
ggtacccggg gatcccggac actggtgacc ttcaaggatg tatttgtgga cttcaccagg    60
gaggagtgga agctgctgga cactgctcag cagatcgtgt acagaaatgt gatgctggag   120
aactataaga acctggtttc cttgggcagc gactacaagg acgacgatga caagtaagct   180
tctcgag                                                            187

<210> SEQ ID NO 25
<211> LENGTH: 277
<212> TYPE: DNA
<213> ORGANISM: Artificial Sequence
```

```
<220> FEATURE:
<223> OTHER INFORMATION: Description of Artificial Sequence: VP16 FLAG

<400> SEQUENCE: 25
ggatccgccc ccccgaccga tgtcagcctg ggggacgagc tccacttaga cggcgaggac      60
gtggcgatgg cgcatgccga cgcgctagac gatttcgatc tggacatgtt ggggacggg     120 gattccccgg ggccgggatt taccccccac gactccgccc cctacggcgc tctggatatg    180
gccgacttcg agtttgagca gatgtttacc gatgcccttg aattgacga gtacggtggg     240 ggcagcgact acaaggacga cgatgacaag taagctt                              277

<210> SEQ ID NO 26
<211> LENGTH: 118
<212> TYPE: DNA
<213> ORGANISM: Artificial Sequence
<220> FEATURE:
<223> OTHER INFORMATION: Description of Artificial Sequence: plasmid
      NF-control

<400> SEQUENCE: 26
gaattcgcta cgccaccat ggcccccaag aagaagagga aggtgggaat ccatggggta       60
cccggggatg gatccggcag cgactacaag gacgacgatg acaagtaagc ttctcgag      118

<210> SEQ ID NO 27
<211> LENGTH: 204
<212> TYPE: DNA
<213> ORGANISM: Artificial Sequence
<220> FEATURE:
<223> OTHER INFORMATION: Description of Artificial Sequence: plasmid
      pGL3-control

<400> SEQUENCE: 27
acgcgtaagc ttgctagcga gcggggagga tcgcggaggc ttggggcagc cgggtagagc      60
gagcggggag gatcgcggag gcttggggca gccgggtaga gcgagcgggg aggatcgcgg    120
aggcttgggg cagccgggta gagcgagcgg ggaggatcgc ggaggcttgg ggcagccggg    180
tagagcgctc agaagcttag atct                                            204

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: linker

<400> SEQUENCE: 28

Asp Gly Gly Gly Ser
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: linker

<400> SEQUENCE: 29

Thr Gly Glu Lys Pro
 1               5

<210> SEQ ID NO 30
<211> LENGTH: 9
<212> TYPE: PRT
```

```
<213> ORGANISM: Artificial Sequence
<220> FEATURE:
<223> OTHER INFORMATION: Description of Artificial Sequence: linker

<400> SEQUENCE: 30

Leu Arg Gln Lys Asp Gly Glu Arg Pro
 1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: linker

<400> SEQUENCE: 31

Gly Gly Arg Arg
 1

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: linker

<400> SEQUENCE: 32

Gly Gly Arg Arg Gly Gly Gly Ser
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: linker

<400> SEQUENCE: 33

Leu Arg Gln Arg Asp Gly Glu Arg Pro
 1               5

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: linker

<400> SEQUENCE: 34

Leu Arg Gln Lys Asp Gly Gly Gly Ser Glu Arg Pro
 1               5                  10

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: linker

<400> SEQUENCE: 35

Leu Arg Gln Lys Asp Gly Gly Gly Ser Gly Gly Gly Ser Glu Arg Pro
 1               5                  10                  15

<210> SEQ ID NO 36
<211> LENGTH: 10
<212> TYPE: DNA
<213> ORGANISM: Artificial Sequence
```

```
<220> FEATURE:
<223> OTHER INFORMATION: Description of Artificial Sequence: target
      sequence

<400> SEQUENCE: 36
gcggtggctc                                                          10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: linker

<400> SEQUENCE: 37

Gln Ser Ser Asp Leu Thr Arg
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: linker

<400> SEQUENCE: 38

Arg Ser Asp Ala Leu Ser Arg
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: linker

<400> SEQUENCE: 39

Arg Ser Asp Glu Arg Lys Arg
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: SV40 large
      T antigen from nuclear localization sequence

<400> SEQUENCE: 40

Pro Lys Lys Lys Arg Lys Val
 1               5

<210> SEQ ID NO 41
<211> LENGTH: 9
<212> TYPE: DNA
<213> ORGANISM: Artificial Sequence
<220> FEATURE:
<223> OTHER INFORMATION: Description of Artificial Sequence: target
      sequence

<400> SEQUENCE: 41 ggggagggc                                                            9

<210> SEQ ID NO 42
<211> LENGTH: 7
<212> TYPE: PRT
<213> ORGANISM: Artificial Sequence
```

```
<220> FEATURE:
<223> OTHER INFORMATION: Description of Artificial Sequence: recognition
      helix

<400> SEQUENCE: 42

Arg Ser Asp His Leu Ala Arg
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: recognition
      helix

<400> SEQUENCE: 43

Arg Ser Asp Asn Leu Ala Arg
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: recognition
      helix

<400> SEQUENCE: 44

Arg Ser Asp His Leu Ser Arg
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: linker

<400> SEQUENCE: 45

Gly Gly Gly Gly Ser
 1               5
```